(12) United States Patent
Rothenberg et al.

(10) Patent No.: US 12,383,719 B2
(45) Date of Patent: Aug. 12, 2025

(54) DISINFECTING CAP WITH RE-USE PREVENTION

(71) Applicant: Becton, Dickinson and Company, Franklin Lakes, NJ (US)

(72) Inventors: Ashley Rachel Rothenberg, Morris Plains, NJ (US); Matthew Oshinski, Oak Ridge, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 87 days.

(21) Appl. No.: 17/229,173

(22) Filed: Apr. 13, 2021

(65) Prior Publication Data
US 2021/0322749 A1 Oct. 21, 2021

Related U.S. Application Data

(60) Provisional application No. 63/131,007, filed on Dec. 28, 2020, provisional application No. 63/011,359, filed on Apr. 17, 2020.

(51) Int. Cl.
*A61M 39/10* (2006.01)
*A61M 39/02* (2006.01)

(52) U.S. Cl.
CPC .... *A61M 39/1011* (2013.01); *A61M 39/0247* (2013.01); *A61M 2039/0258* (2013.01); *A61M 2205/273* (2013.01)

(58) Field of Classification Search
CPC .......... A61M 39/1011; A61M 39/0247; A61M 2039/0258; A61M 2205/273;
(Continued)

(56) References Cited

U.S. PATENT DOCUMENTS 3,403,679 A   10/1968   Sinclair et al.
4,597,758 A   7/1986    Aalto et al.
(Continued)

FOREIGN PATENT DOCUMENTS

CA   2523133 C    2/2013
CN   1322119 A    11/2001
(Continued)

OTHER PUBLICATIONS

"PCT International Search Report and Written Opinion in PCT/US2021/027219 dated Oct. 22, 2021, 22 pages".
(Continued)

*Primary Examiner* — Michael J Tsai
*Assistant Examiner* — Kathleen Paige Farrell
(74) *Attorney, Agent, or Firm* — SERVILLA WHITNEY LLC

(57) ABSTRACT

A medical connector for connection to a corresponding medical connector is described. The medical connector includes a housing having a radial protrusion and a cavity, the cavity defined by a closed end, an open end, a partially cylindrical sidewall and a radial sidewall. The medical connector further includes an insert disposed within the housing, the insert including a locking tab having at least one thread on the inner wall of the locking tab and a recessed notch on the outer wall of the locking tab. The at least one thread of the locking tab engages at least one thread of a corresponding medical connector. Disposed within the cavity, the recessed notch rotates from a first position to a second position, wherein the second position contains a locking structure for non-removably securing the insert to the housing, while allowing for removal of the corresponding medical connector.

13 Claims, 20 Drawing Sheets

(58) Field of Classification Search
CPC ............ A61M 2205/581; A61M 39/20; A61M 2039/1033; A61M 2039/1044; A61M 39/10; A61M 2005/3104; A61M 2005/312; A61M 2039/0288; A61M 5/3202; A61M 39/162; A61M 39/16; A61M 2205/0205; A61M 39/165; A61M 39/18; A61M 2039/0036; A61M 2039/0285; B65D 41/04; F16L 2201/20; F16L 2201/44; B08B 9/023; A61B 90/70; A61J 1/2096; A61J 1/1443; Y10S 604/905

See application file for complete search history.

(56) References Cited

U.S. PATENT DOCUMENTS

| | | | |
|---|---|---|---|
| 4,642,102 | A | 2/1987 | Ohmori |
| 4,711,363 | A | 12/1987 | Marino |
| 4,738,376 | A | 4/1988 | Markus |
| 4,906,231 | A | 3/1990 | Young |
| 5,084,017 | A | 1/1992 | Maffetone |
| 5,496,288 | A | 3/1996 | Sweeney |
| 5,676,406 | A | 10/1997 | Simmons et al. |
| 5,755,696 | A | 5/1998 | Caizza |
| 5,984,123 | A | 11/1999 | Mogami et al. |
| 6,565,529 | B1 | 5/2003 | Kimber et al. |
| 6,632,199 | B1 | 10/2003 | Tucker et al. |
| 7,083,605 | B2 | 8/2006 | Miyahara |
| 8,012,131 | B2 | 9/2011 | Moser et al. |
| 8,388,894 | B2 | 3/2013 | Colantonio |
| 8,647,308 | B2 | 2/2014 | Solomon et al. |
| 8,715,231 | B2 | 5/2014 | Woehr |
| 8,721,627 | B2 | 5/2014 | Alpert et al. |
| 8,777,504 | B2 | 7/2014 | Shaw et al. |
| 8,961,475 | B2 | 2/2015 | Solomon et al. |
| 9,039,989 | B2 | 5/2015 | Lui et al. |
| 9,132,223 | B1 | 9/2015 | Wakeel |
| 9,192,449 | B2 | 11/2015 | Kerr et al. |
| 10,099,048 | B2 | 10/2018 | Chiu et al. |
| 10,166,381 | B2 | 1/2019 | Gardner et al. |
| 10,376,686 | B2 | 8/2019 | Burkholz et al. |
| 10,589,080 | B2 | 3/2020 | Hitchcock et al. |
| 10,603,481 | B2 | 3/2020 | Avula et al. |
| 10,871,246 | B2 | 12/2020 | Marici et al. |
| 11,353,147 | B2 | 6/2022 | Marici |
| 11,511,100 | B2 | 11/2022 | Ryan |
| 11,628,288 | B1* | 4/2023 | Soloman et al. ...... A61M 39/18 |
| 2003/0093009 | A1 | 5/2003 | Newby et al. |
| 2003/0209681 | A1 | 11/2003 | Leinsing et al. |
| 2004/0039341 | A1 | 2/2004 | Ranalletta |
| 2004/0044318 | A1 | 3/2004 | Fiser et al. |
| 2005/0147525 | A1 | 7/2005 | Bousquet |
| 2005/0197646 | A1* | 9/2005 | Connell et al. ........ A61M 39/20 |
| 2007/0060904 | A1 | 3/2007 | Vedrine et al. |
| 2007/0129705 | A1 | 6/2007 | Trombley, III et al. |
| 2008/0010766 | A1 | 1/2008 | Kaufman et al. |
| 2008/0171995 | A1 | 7/2008 | Mtullo et al. |
| 2008/0177250 | A1 | 7/2008 | Howlett et al. |
| 2010/0000040 | A1 | 1/2010 | Shaw et al. |
| 2010/0049170 | A1 | 2/2010 | Solomon et al. |
| 2010/0050351 | A1 | 3/2010 | Colantonio et al. |
| 2010/0100056 | A1 | 4/2010 | Cawthon et al. |
| 2011/0046603 | A1 | 2/2011 | Felsovalyi et al. |
| 2011/0054440 | A1 | 3/2011 | Lewis |
| 2011/0213341 | A1 | 9/2011 | Solomon et al. |
| 2011/0264037 | A1 | 10/2011 | Foshee et al. |
| 2012/0039764 | A1 | 2/2012 | Solomon et al. |
| 2012/0111368 | A1 | 5/2012 | Rahimy et al. |
| 2012/0123386 | A1 | 5/2012 | Tsals |
| 2012/0302997 | A1 | 11/2012 | Gardner et al. |
| 2013/0085474 | A1 | 4/2013 | Charles et al. |
| 2013/0171030 | A1 | 7/2013 | Ferlic et al. |
| 2013/0197485 | A1 | 8/2013 | Gardner et al. |
| 2013/0338644 | A1 | 12/2013 | Solomon et al. |
| 2014/0052074 | A1 | 2/2014 | Tekeste |
| 2014/0150832 | A1 | 6/2014 | Rogers et al. |
| 2014/0191501 | A1* | 7/2014 | Brugger et al. ... A61M 39/1011 |
| 2014/0366914 | A1 | 12/2014 | Kerr et al. |
| 2015/0094666 | A1 | 4/2015 | Bates et al. |
| 2016/0045629 | A1 | 2/2016 | Gardner et al. |
| 2016/0067422 | A1 | 3/2016 | Davis et al. |
| 2016/0158520 | A1 | 6/2016 | Ma et al. |
| 2017/0203087 | A1 | 7/2017 | Ryan et al. |
| 2018/0085568 | A1 | 3/2018 | Drmanovic |
| 2018/0200145 | A1 | 7/2018 | Sanders et al. |
| 2018/0200500 | A1 | 7/2018 | Ziebol et al. |
| 2018/0237190 | A1 | 8/2018 | Iwasaki |
| 2018/0243547 | A1 | 8/2018 | Fox et al. |
| 2018/0256879 | A1 | 9/2018 | Chiu et al. |
| 2018/0256883 | A1* | 9/2018 | Follman ............... A61M 39/162 |
| 2019/0001115 | A1* | 1/2019 | Ma ...................... A61M 39/162 |
| 2019/0151643 | A1 | 5/2019 | Alpert |
| 2019/0234540 | A1* | 8/2019 | Marici .................. A61M 39/20 |
| 2019/0308006 | A1 | 10/2019 | Erekovcanski et al. |
| 2019/0351212 | A1 | 11/2019 | Dudar et al. |
| 2020/0147360 | A1* | 5/2020 | Arnett ................ A61M 39/1011 |
| 2020/0238070 | A1 | 7/2020 | Ryan |
| 2021/0100996 | A1* | 4/2021 | Wijesuriya et al. ......... A61M 39/0247 |
| 2021/0187267 | A1 | 6/2021 | Jiang |
| 2022/0273931 | A1 | 9/2022 | Jiang et al. |
| 2023/0080687 | A1 | 3/2023 | Ryan |

FOREIGN PATENT DOCUMENTS

| | | |
|---|---|---|
| CN | 101541361 A | 9/2009 |
| CN | 101631585 A | 1/2010 |
| CN | 101980746 A | 2/2011 |
| CN | 201807018 U | 4/2011 |
| CN | 102188766 A | 9/2011 |
| CN | 102448502 A | 5/2012 |
| CN | 103025374 A | 4/2013 |
| CN | 103083767 A | 5/2013 |
| CN | 204161736 U | 2/2015 |
| CN | 206198472 U | 5/2017 |
| CN | 216022674 U | 3/2022 |
| DE | 10247963 A1 | 5/2004 |
| DE | 202005004079 U1 | 7/2006 |
| EP | 0589379 A1 | 3/1994 |
| EP | 2606930 A1 | 6/2013 |
| EP | 2832391 A1 | 2/2015 |
| EP | 3275490 A1 | 1/2018 |
| GB | 2408259 A | 5/2005 |
| GB | 2518646 A | 4/2015 |
| JP | S5841561 A | 3/1983 |
| JP | H03139363 A | 6/1991 |
| JP | H04501672 A | 3/1992 |
| JP | 2001502191 A | 2/2001 |
| JP | 2001521792 A | 11/2001 |
| JP | 2004208740 A | 7/2004 |
| JP | 2008532701 A | 8/2008 |
| JP | 2008239164 A | 10/2008 |
| JP | 2008253775 A | 10/2008 |
| JP | 2009526241 A | 7/2009 |
| JP | 2010527276 A | 8/2010 |
| JP | 2012522593 A | 9/2012 |
| JP | 2013509274 A | 3/2013 |
| JP | 2015517377 A | 6/2015 |
| JP | 2016511119 A | 4/2016 |
| JP | 2016104214 A | 6/2016 |
| WO | 0019878 | 4/2000 |
| WO | 200024442 A1 | 5/2000 |
| WO | 200224551 A1 | 3/2002 |
| WO | 2011066586 A1 | 6/2011 |
| WO | 2012144026 A1 | 10/2012 |
| WO | 2013046857 A1 | 4/2013 |
| WO | 2014159346 A1 | 10/2014 |
| WO | 2015004728 A1 | 1/2015 |
| WO | 2015127285 A1 | 8/2015 |
| WO | 2015174953 A1 | 11/2015 |
| WO | 2016158144 A1 | 10/2016 |
| WO | 2017087400 A1 | 5/2017 |
| WO | 2017095373 A1 | 6/2017 |

(56) References Cited

FOREIGN PATENT DOCUMENTS

| | | |
|---|---|---|
| WO | 2018106508 A1 | 6/2018 |
| WO | 2018237090 A1 | 12/2018 |
| WO | 2019147906 A1 | 8/2019 |
| WO | 2019212637 A1 | 11/2019 |
| WO | 2020056120 A1 | 3/2020 |
| WO | 2020112767 A1 | 6/2020 |

OTHER PUBLICATIONS

Non-Final Office Action in U.S. Appl. No. 16/774,853 dated Feb. 1, 2022, 12 pages.
"Non-Final Office Action in U.S. Appl. No. 17/076,102 dated Aug. 24, 2021, 10 pages".
PCT Invitation to Pay Additional Fees in PCT/US2021/019546, mailed on Jun. 15, 2021, 17 pages.
PCT International Search Report and Written Opinion in PCT/US2021/027214 dated Jul. 19, 2021, 14 pages.
PCT International Search Report and Written Opinion in PCT/US2021/027218 dated Jul. 22, 2021, 14 pages.
PCT International Search Report and Written Opinion in PCT/US2021/027220 dated Jul. 21, 2021, 15 pages.
PCT Invitation to Pay Additional Fees in PCT/US2021/027219, mailed on Jul. 22, 2021, 15 pages.
"Ruhof Dry Sponges", Ruhof, Sep. 30, 2016, https://www.ruhof.com/products/ruhof-dry-sponges (Year: 2016).

\* cited by examiner

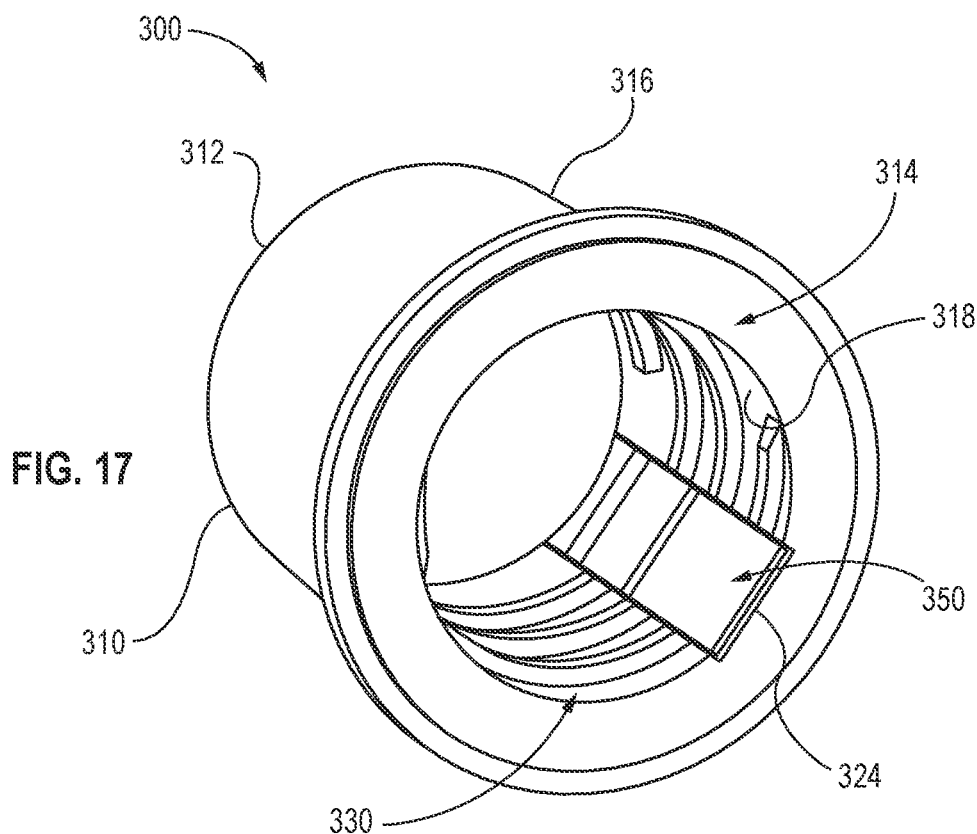
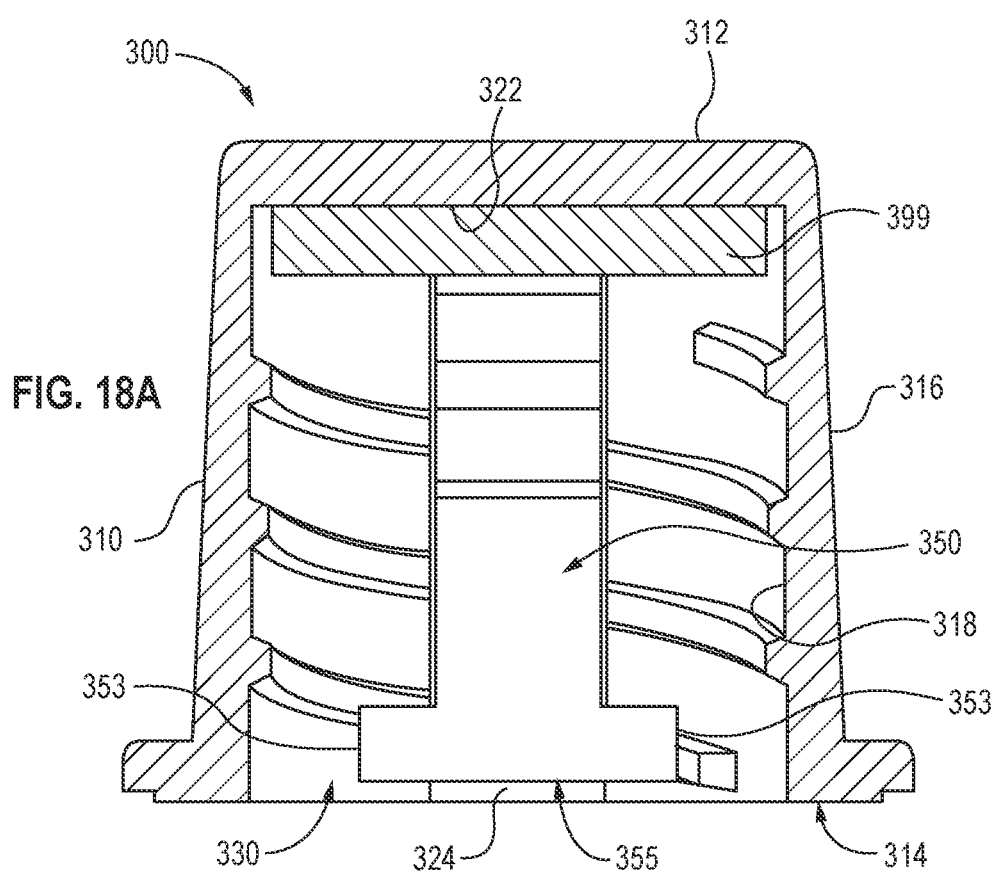

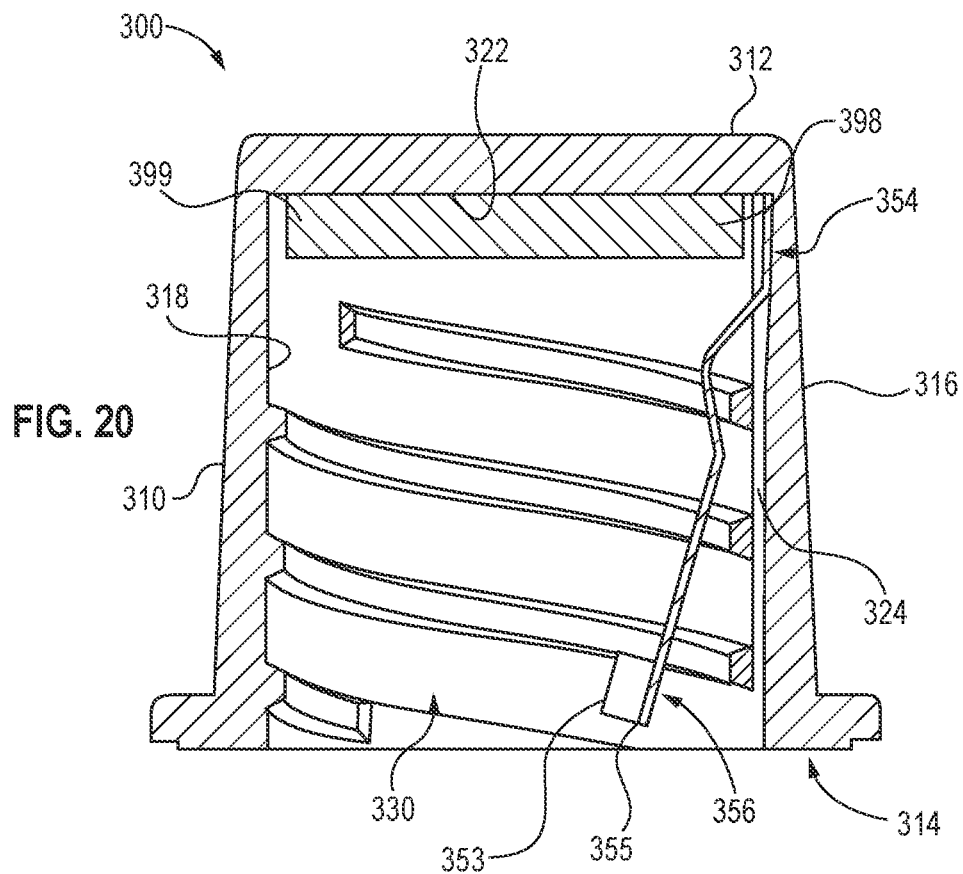
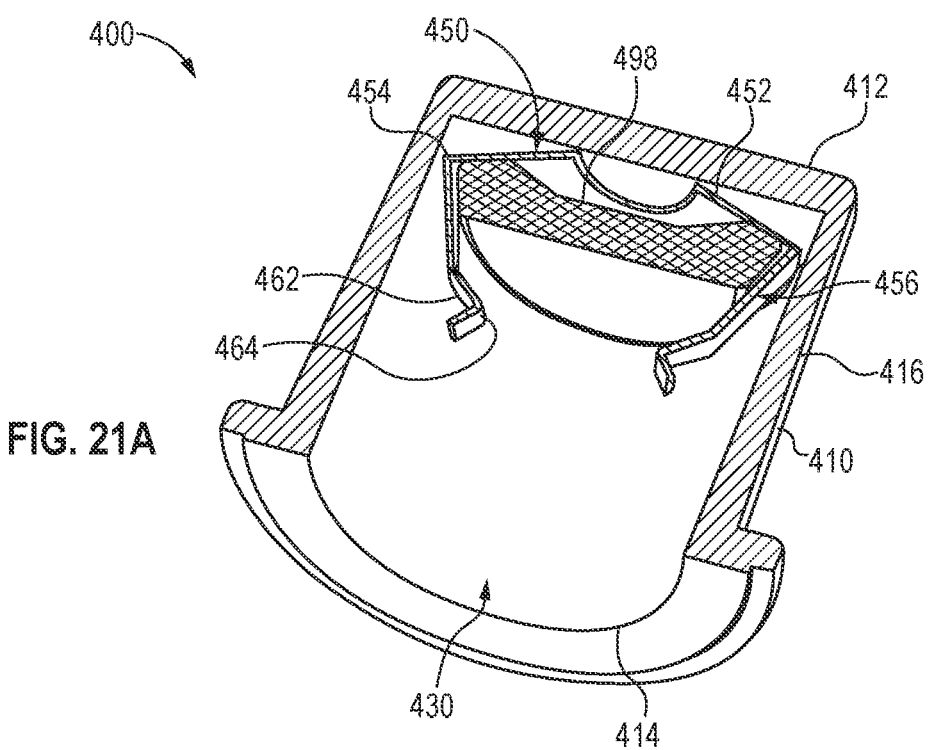

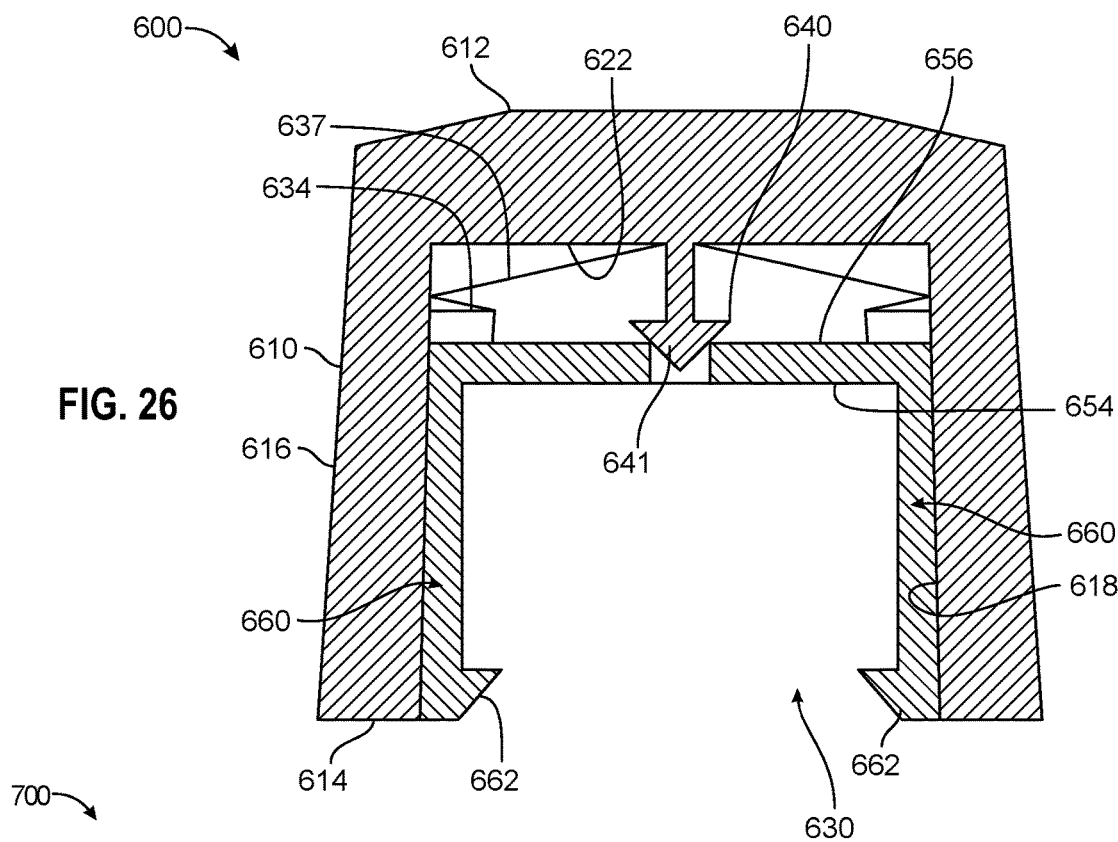
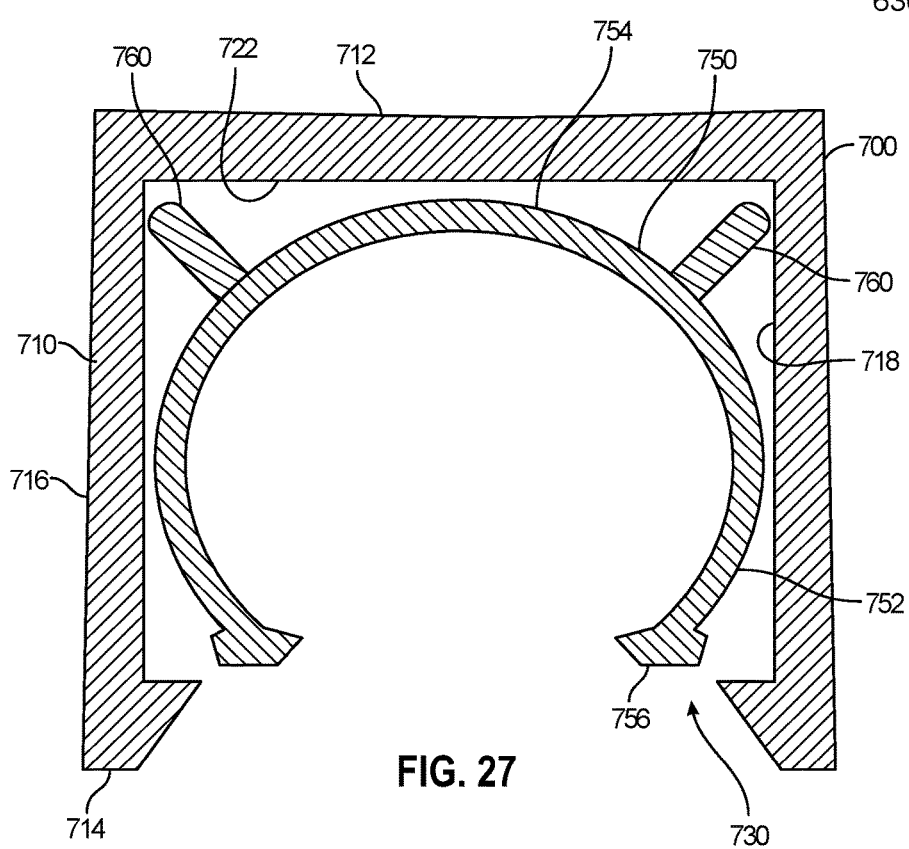

DISINFECTING CAP WITH RE-USE PREVENTION

CROSS-REFERENCE TO RELATED APPLICATIONS

This application claims priority to U.S. Provisional Application No. 63/011,359, filed Apr. 17, 2020, and U.S. Provisional Application No. 63/131,007, filed Dec. 28, 2020, the entire disclosures of which are hereby incorporated by reference herein.

TECHNICAL FIELD

The present disclosure generally relates to medical connectors. In particular, the present disclosure relates to mating elements of medical connectors having re-use prevention features and disinfection features.

BACKGROUND

Vascular access devices (VAD's) are commonly used therapeutic devices and include intravenous (IV) catheters. There are two general classifications of VAD's: peripheral catheters and central venous catheters. Bacteria and other microorganisms may gain entry into a patient's vascular system from access hubs and ports/valves upon connection to the VAD when delivering fluids or pharmaceuticals to a patient. Each access hub, connection, port or valve is associated with some risk of transmitting a catheter related bloodstream infection (CRBSI), which can be costly and potentially lethal.

In order to decrease CRBSI cases and to ensure VAD's are used and maintained correctly, standards of practice have been developed, which include disinfecting and cleaning procedures.

Disinfection caps have been added to the Society for Healthcare Epidemiology of America (SHEA) guidelines and have also been incorporated into the Infusion Nurses Standards (INS) guidelines.

In developed markets, when utilizing an IV catheter, a needleless connector will typically be used to close off the system and then subsequently accessed to administer medication or other necessary fluids via the catheter to the patient. INS Standards of Practice recommend the use of a needleless connector and state that it should be "consistently and thoroughly disinfected using alcohol, tincture of iodine or chlorhexidine gluconate/alcohol combination prior to each access." The disinfection of the needleless connector is ultimately intended to aid in the reduction of bacteria that could be living on the surface and possibly lead to a variety of catheter related complications including CRBSI. Nurses will typically utilize a 70% isopropyl alcohol (IPA) pad to complete this disinfection task by doing what is known as "scrubbing the hub." However, compliance and the level of disinfection attributed to this practice typically relies on the ability and competency of the user. In addition to a lack of compliance to "scrubbing the hub", it has also been noted through clinician interviews that there is often a variation in scrub time, dry time and the number of times the needleless connector is scrubbed.

Threaded needleless connectors are used to decrease CRBSI cases and to ensure VAD's are used and maintained properly as threaded connectors are more secure than slip connectors. However, while threaded needleless connectors, such a threaded luer connectors, are more secure, they require more manipulation by the clinician and the connection is not as quick as luer slip connectors Thus, there is a need for medical connectors capable of disinfecting luer connectors and reuse prevention thereby reducing risk of the disinfectant entering the blood stream. Further, there is a need for devices which mate with medical connectors which provide for the security of threaded connectors but the ease of use of slip-connectors.

SUMMARY

One aspect of the present disclosure pertains to medical connectors and mating elements of a medical connector (i.e., a needleless connector) having a housing, a locking structure and an insert disposed within the medical connector. The housing has a substantially cylindrical housing body having a radial protrusion extending from the cylindrical housing body and a cavity defined by a closed end, an open end, a partially cylindrical inner sidewall of the housing body and a radial sidewall of the radial protrusion. In some embodiments, the closed end further includes a lumen for the transfer of fluid beyond the closed end. The locking structure is disposed on a lateral portion of the radial sidewall of the cavity, the locking structure including a sloped tab. The insert is advanced into the cavity of the housing, the insert comprising a discoid body having a distal surface, a proximal surface, a sidewall and a locking tab extending proximally from the sidewall, the insert includes at least one thread on an inner wall of the locking tab and a recessed notch disposed on a distal portion of an outer wall of the locking tab.

In one or more embodiments, the insert rotates from a first position to a locking position, the first position being defined by a medial portion of the radial sidewall and the locking position being defined by the lateral portion, the lateral portion including the locking structure. In one or more embodiments, the recessed notch engages a ledge of the sloped tab when the recessed notch is advanced past the sloped tab. In one or more embodiments, the locking tab elastically deforms.

In one or more embodiments, the locking structure further includes an outwardly sloped surface which slopes outwardly from a medial or leftward position to a lateral or rightward position.

In one or more embodiments, the outwardly sloped surface extends at least partially a length of the arc of the radial sidewall. In one or more embodiments, the outwardly sloped surface extends an entire length of the arc of the radial sidewall.

In one or more embodiments, the sloped tab extends from a lateral portion of the outwardly sloped surface. In one or more embodiments, the outwardly sloped surface causes deformation of the locking tab.

In one or more embodiments, the locking structure further includes a proximally sloped surface, the proximally sloped surface located adjacent to a ledge of the sloped surface.

In one or more embodiments, the proximally sloped surface slopes inwardly with respect to the radial sidewall from a distal position to a proximal position.

In one or more embodiments, the distal surface of the insert abuts an inner top surface of the cavity of the housing when the insert is fully advanced into the cavity.

In one or more embodiments, the medical connector further comprises an absorbent material disposed between the distal surface of the insert and an inner top surface of the cavity of the housing when the insert is fully advanced into the cavity. In one or more embodiments, the absorbent material contains a disinfectant.

In one or more embodiments, fully advancing the insert into the cavity in a distal direction causes the distal surface of the insert and the inner top surface of the cavity of the housing to compress the absorbent material, the absorbent material releasing the disinfectant. Disinfectant evacuates into the cavity by a gap defined by the partially cylindrical inner sidewall of the housing and the sidewall of the insert.

In one or more embodiments, the diameter of the partially cylindrical inner sidewall of the housing has a larger diameter than the sidewall of the insert.

In one or more embodiments, a retention tab is disposed on an inner top surface of the housing, the inner top surface non-removably securing an aperture disposed on the distal surface of the insert, the aperture extending therethrough.

A second aspect of the present disclosure pertains to a medical connector having a housing, a locking structure and an insert disposed within medical connector. The housing has a substantially cylindrical housing body having a radial protrusion extending from the cylindrical housing body and a cavity defined by a closed end, an open end, a partially cylindrical inner sidewall of the housing body and a radial sidewall of the radial protrusion. The locking structure is disposed on a lateral portion of the radial sidewall of the cavity, the locking structure including a sloped tab. The insert is advanceable into the cavity of the housing, the insert comprising a discoid body having a distal surface, a proximal surface, a sidewall and a locking tab extending proximally from the sidewall, the insert including at least one thread on an inner wall of the locking tab and a recessed notch disposed on a distal portion of an outer wall of the locking tab. Threading a corresponding medical connector into the cavity causes the insert to be advanced into the cavity, the corresponding medical connector having at least one thread to engage the at least one thread of the insert.

In one or more embodiments, the corresponding medical connector is removably threaded into the cavity.

A third aspect of the present disclosure pertains to a medical connector of a syringe having a housing protruding in a distal direction from a distal wall of a syringe barrel of the syringe, the housing including a cavity defined by the distal wall of the syringe barrel, an open end opposite the distal wall and a partially cylindrical sidewall extending from the distal wall to the open end, the housing further including a radial sidewall defined by a radial protrusion extending laterally from the housing, the radial protrusion and the radial sidewall being in the shape of a laterally protruding arc.

The syringe further comprises a tapered hub disposed within the cavity of the housing, the tapered hub extending in a distal direction from the distal wall of the syringe barrel, the tapered hub configured to interdigitate with a corresponding cavity of a housing of a vascular access device.

The syringe further comprises a locking structure disposed on the radial sidewall including an outwardly sloped surface, and a sloped tab, the sloped surface slopes outwardly from a medial or leftward position to a lateral or rightward position, the outwardly sloped surface extending at least partially the length of the arc of the radial sidewall, the sloped tab slopes outwardly from a lateral or rightward position to a medial or leftward position, the sloped tab including a ledge formed by a wall at a substantially right angle with respect to the radial sidewall.

The syringe further comprises an insert having a generally discoid body, the discoid body having a proximal surface, a distal surface a sidewall, a locking tab and an aperture, the locking tab extending from the distal surface, the aperture is disposed on the proximal surface of the discoid body and extends therethrough, the insert further includes at least one thread is disposed on the inner wall of the locking tab.

A first position is defined by the medial or leftward portion of the radial sidewall and a locking position is defined by the sloped tab and the ledge. The housing is configured as a medical connector able to receive a male luer fitting of a vascular access device. When the insert is advanced proximally into the cavity of the housing, the locking tab is disposed in the first position causing the locking tab insert to elastically deform outwardly with respect to the radial sidewall. When the insert rotationally approaches the locking position, the outwardly sloped surface further elastically deforms the locking tab inward until the recessed notch passes the ledge of the radial sidewall, when the notch has passed the ledge and the notch non-releasably engages the ledge, thereby preventing medial or leftward movement of the locking tab.

A third embodiment of the present disclosure pertains to a medical connector comprising a substantially cylindrical housing having a distal wall, a proximal open end, an inner sidewall extending between the distal wall to the open end and a cavity. At least one helical thread disposed on an inner sidewall of the cavity. A channel is disposed on the inner sidewall having a substantially rectangular profile extending from the distal wall to the open end. An absorbent material abutting an inner distal surface of the housing The medical connector further comprises a leaf spring disposed within the channel, the leaf spring having a rectangular cross-section and an arc, the arc is between a distal portion and a proximal portion, the distal portion is non-removably attached to the channel, the proximal portion abutting the channel in an initial state.

Upon advancement of a corresponding medical connector into the cavity, at least one thread of the corresponding medical connector depresses the arc of the spring into the channel causing the proximal portion of the spring to defect away from the channel defining a final state; A proximal end of the proximal portion of the spring engages a lower segment of the least one thread of the corresponding medical connector, thereby locking the corresponding medical connector within the cavity in a threaded fit and an interference fit A fourth embodiment of the present disclosure relates to a medical connector comprising a substantially cylindrical housing having a distal wall, a proximal open end, an inner distal surface and a cavity defined by the proximal open end and the closed distal end. The medical connector further comprises a cupped spring comprising a frusto-conical shaped disk body having at least two prongs extending from a proximal edge of the disk body, the at least two prongs extending from a proximal edge of the disc body in a proximal direction, each of the at least two prongs comprise a proximal portion and a distal portion adjacent to the proximal portion, the distal portion forming a medial hook extending toward a center of the disk body, the medial hook comprising a medial edge configured to engage with a corresponding thread of a corresponding medical connector. The medical connector further comprises an absorbent material abutting an inner distal surface of the housing.

Advancement of the corresponding medical connector into the cavity causes the disk body to deform inward, pushing the proximal edge of the disk body against a lower segment of the least one thread of the corresponding medical connector, thereby locking the corresponding medical connector within the cavity.

A fifth embodiment of the present disclosure relates to a medical connector comprising a substantially cylindrical housing having a distal wall, a proximal open end, an inner sidewall extending between the distal wall to the open end and a cavity. At least one helical thread disposed on an inner sidewall of the cavity, the helical thread having a distal portion unitarily formed onto the inner sidewall and a frangible portion proximal to the distal portion configured to detach and cross-thread upon threading and advancing a corresponding thread of a corresponding medical connector into the cavity. An absorbent material abutting an inner distal surface of the housing A sixth embodiment of the present disclosure relates to a medical connector comprising a substantially cylindrical housing having a distal wall, a proximal open end, a sidewall extending between the distal wall to the open end, a cavity extending from the open end to the distal wall, an inner distal surface, and at least one tooth extending medially into the cavity from an inner sidewall of the housing, the at least one tooth positioned a distance from the inner distal surface of the housing.

The medical connector further comprises an insert in the shape of a discoid body, the discoid body having a proximal surface and a distal surface, at least two locking tabs extending from the distal surface in a distal direction away from the distal surface, each of the at least two locking tabs having a hooked proximal end configured to interlock with corresponding thread of a corresponding medical connector, and a plurality of ridges disposed on a sidewall of the discoid body, the plurality of ridges configured to interdigitate with the least one tooth of the housing. An absorbent material abuts the inner distal surface of the distal wall of the housing.

A seventh aspect of the present disclosure relates to a medical connector comprising a substantially cylindrical housing having a distal wall, a proximal open end, a sidewall extending between the distal wall to the open end and a cavity. The medical connector further comprises an insert in the shape of a C-shaped body having a distal end in the form of an arc and an open proximal end, and two living hinges extending from the distal end. An absorbent material abuts the inner distal surface of the distal wall of the housing.

Advancement of a corresponding medical connector into the cavity causes deflection of the c-shaped body, thereby locking the open proximal end against threads of a corresponding medical connector.

An eighth aspect of the present disclosure relates to a medical connector comprising a substantially cylindrical housing having a distal wall, a proximal open end, a sidewall extending between the distal wall to the open end and a cavity, an inner distal surface, a medial wall positioned a distance from the inner distal surface of the housing.

The medical connector further comprises an insert in the shape of a C-shaped body having a distal portion in the form of an arc, an open proximal portion and at least two living hinges extending tangential to the distal portion. An absorbent material abuts the inner distal surface of the distal wall of the housing. Advancement of a corresponding medical connector into the cavity causes deflection of the insert, thereby locking the open proximal end against threads of the medical connector. The medial wall further includes an aperture configured to receive the distal portion of the insert.

BRIEF DESCRIPTION OF THE DRAWINGS

FIG. 17 illustrates a perspective view of a housing of a medical connector in accordance with a third embodiment of the present disclosure.

FIG. 18A illustrates a cross-sectional view of the housing in an initial state in accordance with the third embodiment as shown in FIG. 17;

FIG. 20 illustrates a cross-sectional view of the housing in the final state in accordance with the third embodiment as shown in FIG. 17;

FIG. 21A illustrates a cross-sectional view of a housing in an initial state in accordance with a fourth embodiment of the present disclosure;

FIG. 26 illustrates a cross-sectional view of the insert of FIGS. 25A and 25B disposed within a housing of an exemplary medical connector in accordance with the sixth embodiment of the present disclosure;

FIG. 27 illustrates a cross-sectional view of an insert disposed within a housing of an exemplary medical connector in accordance with a seventh embodiment of the present disclosure.

DETAILED DESCRIPTION

Figure 1A:
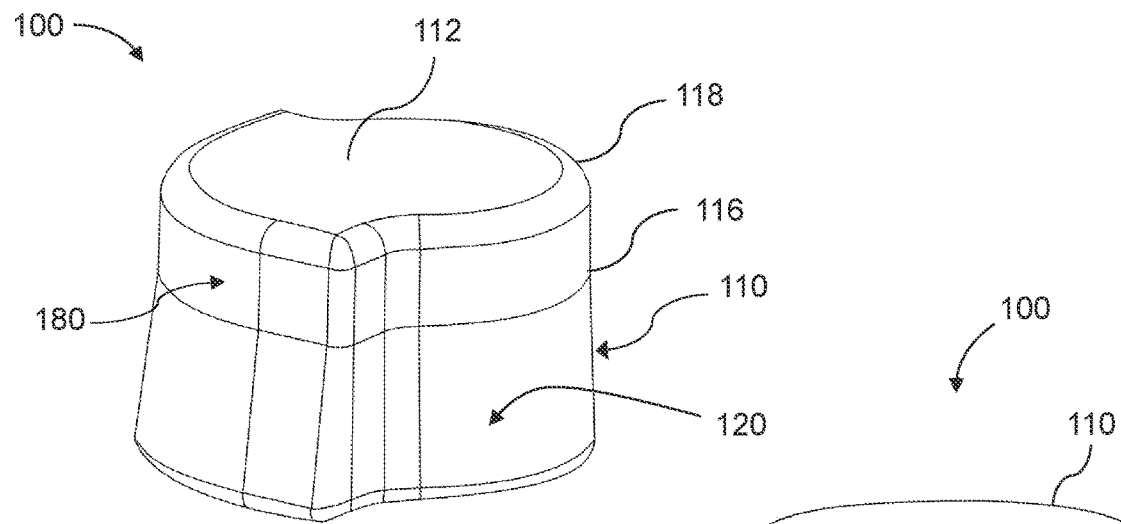
FIG. 1A illustrates a perspective view of a housing of a medical connector assembly according to a first exemplary embodiment of the disclosure.

Embodiments of the disclosure pertain to a sterile, medical connector for connection to and disinfection of a corresponding medical connector having an open lumen, including male, female needleless connectors, luer connectors, and stopcocks. In some embodiments, the medical connectors can male or female luer connectors. In some embodiments, the medical connector can be a cap or a connector of a syringe. In some embodiments, the medical connectors of the present disclosure are incorporated in medical devices. In some embodiments, the medical connectors of the present disclosure are mating elements incorporated in medical devices. Embodiments of the medical connector comprise a housing, an insert and an absorbent material, the insert and absorbent material disposed within the housing. Upon inserting a corresponding medical connector into the housing, the corresponding medical connector is advanced against the housing and insert which compresses the absorbent material thereby releasing antimicrobial disinfectant fluid or gel (hereinafter "disinfectant"), and in some embodiments, prevents reuse of the medical connector and the corresponding medical connector. The disinfectant disinfects the corresponding medical connector. In one or more embodiments, the medical connector and corresponding medical connector as described in detail below has the means to be of a single use, wherein the insert of the medical connector non-releasably locks onto the housing of the medical connector.

The housing comprises a substantially cylindrical body having a radial protrusion and a cavity defined by a closed end, an open end, a partially cylindrical inner sidewall of the housing and a radial sidewall of the radial protrusion. The inner sidewall of the housing having a length $L_C$ extending from the closed end to a distal wall. In one or more embodiments, the open end includes an engagement surface wherein a peelable seal is attached to.

In one or more embodiments, the insert includes an inner wall. In one or more embodiments, the inner wall of the insert has at least one thread adapted to engage a female luer connector. The medical connector provides a mechanical barrier for connectors and contains an antimicrobial agent for disinfection. The medical connector of the present disclosure also allows the practitioner to streamline the disinfecting process while blocking the lumen of open luers to facilitate the mitigation of the ingress of contaminants and disinfectant into the open lumens of the connectors, thereby reducing risk of the contaminants and disinfectant entering the blood stream.

With respect to terms used in this disclosure, the following definitions are provided.

As used herein, the use of "a," "an," and "the" includes the singular and plural.

As used herein, the term "catheter related bloodstream infection" or "CRBSI" refers to any infection resulting from the presence of a catheter or IV line.

As used herein, the terms "medical connector" and "corresponding medical connector" refer to needleless and needle-free medical connectors such as BD MAXPLUS, BD MAXZERO™, STARTSITE™, NEUTRACLEAR™, BD Q-SYTE™ by BECTON DICKENSON AND COMPANY®. Furthermore, the terms "medical connector" and "corresponding medical connector" refer to sterile connectors having a male or female open lumen, luer connectors, and stopcocks. The terms "medical connector" and "corresponding medical connector" also refer to mating elements of needleless and needle-free connectors and can be incorporated into medical devices which connect to medical connectors, such as a cap or a connector of a syringe. The medical connector can include elements which connect or mate to the corresponding medical connector, such as a male medical connector having elements which mate to a corresponding female medical connector.

As used herein, the term "needleless connector" and "corresponding needleless connector" refer to a male and female connector combination. Where the needleless connector is a male needleless connector, the corresponding needleless connector is a female needleless connector. Likewise, where the needleless connector is a female needleless connector, the corresponding needleless connector is a male needleless connector. The needleless connector can be a cap, a connector of a syringe, a connector of a vascular access device, a connector of a stopcock, a luer connector with a corresponding open luer connector, a connector having a valve, a connector lacking a valve, a manifold port, stopcock, any conventional medical device having needleless connectors, or a regular open luer connector.

As used herein, the term "Luer connector" refers to a connection collar that is the standard way of attaching syringes, catheters, hubbed needles, IV tubes, etc. to each other. The Luer connector consists of male and female interlocking tubes, slightly tapered to hold together better with even just a simple pressure/twist fit. Luer connectors can optionally include an additional outer rim of threading, allowing them to be more secure. The Luer connector male end is generally associated with a flush syringe and can interlock and connect to the female end located on the vascular access device (VAD). Luer connector also has a distal end that releasably attaches the Luer connector to the hub of a VAD, and a proximal end that releasably attaches the Luer connector to the barrel of a syringe.

As used herein, ISO 80369-7:2016 defines a specification for standard Luer connectors including a 6% taper between the distal end and the proximal end. A male standard luer connector increases from the open distal end to the proximal end. A female standard luer connector decreases from the open proximal end to the distal end. According to ISO 80369-7:2016, a male standard luer connector has an outer cross-sectional diameter measured 0.75 mm from the distal end of the tip of between 3.970 mm and 4.072 mm. The length of the male standard luer taper is between 7.500 mm to 10.500 mm. The outer cross-sectional diameter measured 7.500 mm from the distal end of the tip is between 4.376 mm and 4.476 mm. As used herein, the phrases "male standard luer connector" and "female standard luer connector" shall refer to connectors having the dimensions described in ISO 80369-7, which is hereby incorporated by reference in its entirety.

As would be readily appreciated by skilled artisans in the relevant art, while descriptive terms such as "lock", "tip", "hub", "thread", "sponge", "prong", "protrusion/insert", "tab", "slope", "wall", "top", "side", "bottom" and others are used throughout this specification to facilitate understanding, it is not intended to limit any components that can be used in combinations or individually to implement various aspects of the embodiments of the present disclosure.

The matters exemplified in this description are provided to assist in a comprehensive understanding of exemplary embodiments of the disclosure. Accordingly, those of ordinary skill in the art will recognize that various changes and modifications of the embodiments described herein can be made without departing from the scope and spirit of the disclosure. Also, descriptions of well-known functions and constructions are omitted for clarity and conciseness.

In one or more exemplary implementation of the embodiments of present disclosure, the medical connector is in the form of a cap having mating elements which connect to a corresponding medical connector, such as threads, a tab or a flange. The cap comprising a housing and an insert. The insert of the cap, connector cap or disinfecting cap includes at least one thread and other features in any and all combinations allowing it to interface with a corresponding thread or plurality of threads of female threaded fittings.

According to further exemplary implementations of the embodiments of the present disclosure, configuration of structural elements making up the insert include a tab protruding from the insert, the tab comprising at least one thread to connect to the corresponding thread or plurality of threads of corresponding medical connectors.

According to still further exemplary implementations of the embodiments of the present disclosure, female threads are sized and have a thread pattern that will engage with a standard ISO594-2 type of male fitting and/or a male threads that are sized and have a thread pattern that will engage with a standard ISO594-2 type of female fitting. An example of an ISO594-2 type of fitting is a Q-style fitting.

According to still further exemplary implementations of the embodiments of the present disclosure, the tab of the insert may bend or elastically deform in order to allow better interference fit compliance with the fittings.

In one or more embodiments, the female medical connector may be selected from the group consisting essentially of needle-free connectors, catheter luer connectors, stopcocks, and hemodialysis connectors. In one or more embodiments, the medical connector is selected from a Q-Syte connector, MaxPlus, MaxPlus Clear, MaxZero, UltraSite, Caresite, InVision-Plus, Safeline, OneLink, V-Link, ClearLink, NeutraClear, Clave, MicroClave, MicroClave Clear, Neutron, NanoClave, Kendall, Nexus, InVision, Vadsite, Bionector, etc.

In one or more embodiments, the male medical connector may be an intravenous tubing end or a stopcock. In some embodiments, the medical connectors described are configured to receive slip connectors such as luer slip connectors. In some embodiments, the medical connectors described include one or more engagement elements such as teeth or c-clips which are configured to engage onto threaded connectors and slip connectors by advancing the threaded connector or slip connector into the medical connector. In some embodiments, the medical connectors described can engage with threaded connectors, such as threaded luer connectors, only by advancement of the threaded connector into the medical connector without requiring the clinician to thread, rotate, or torque the threaded connector or its mating element.

In some embodiments, the teeth or c-clips further comprise a set of tabs protruding from a distal end of the teeth or c-clips. In a fully advanced position, the set of tabs interlock with a thread of a corresponding medical connector. The set of tabs engage the thread of the needleless connector to non-removably lock the corresponding medical connector. In some embodiments, the set of tabs is wider than the spring. In some embodiments, the set of tabs is configured to de-thread from the corresponding thread and jump off the thread path to prevent re-use.

In some embodiments, upon full advancement of a corresponding threaded medical connector the medical connector of embodiments described herein are configured to create an audible click or sound detectable by either the clinician or ancillary detection systems.

Before describing several exemplary embodiments of the disclosure, it is to be understood that the disclosure is not limited to the details of construction or process steps set forth in the following description. The disclosure is capable of other embodiments and of being practiced or being carried out in various ways.

Referring now to the drawings, wherein like reference numerals designate identical or corresponding parts throughout the several views, embodiments of the present disclosure are described as follows.

Figure 1B:
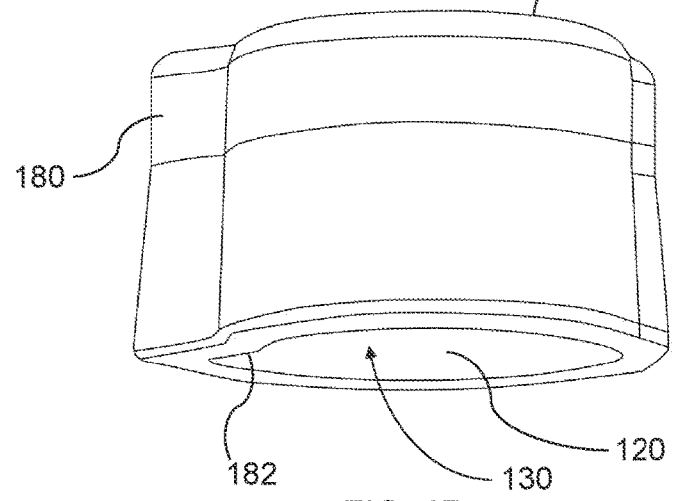
FIG. 1B illustrates a perspective side view of a housing body of the medical connector in accordance with the embodiment as shown in FIG. 1.

A first aspect of the present disclosure relates to a housing 110 of a medical connector 100. As shown in FIGS. 1A and 1B, the medical connector is in the form of a cap. In some embodiments, the housing 110 pertains to elements which connect or mate to a corresponding medical connector. The housing 110 of the medical connector 100 is of a partially cylindrical shape which is integral with a radial protrusion 180, the radial protrusion 180 being in the form of a protruding arc. The angle of the protruding arc ranges from 10 degrees to 350 degrees. The housing 110 includes a cavity defined by a closed end 112, an open end 114 and a partially cylindrical inner sidewall 120. The partially cylindrical inner sidewall 120 is integral with a radial sidewall 182. The radial protrusion 180 includes a first sidewall 181A and a second sidewall 181B. The radial sidewall 182 of the housing 110 includes a locking structure described in further detail below.

The closed end 112 is in a distal location and the open end 114 is in a proximal location relative to the closed end 112. In one or more embodiments, the partially cylindrical inner sidewall 120 has a substantially constant diameter DB. In one or more embodiments, the partially cylindrical inner sidewall 120 can further be outwardly tapered, wherein the taper increases proximally towards the open end 114. A corresponding medical connector is received through the open end 114 into the cavity 130.

The housing 110 further includes an outer sidewall 116. The outer sidewall 116 in the depicted embodiment has partially cylindrical shape with a smooth surface and a chamfer 118. In one or more embodiments, the chamfer 118 may be rounded. In one or more embodiments the chamfer 118 may extend partially around the outer sidewall 116. In one more embodiments, the outer sidewall 116 may have a plurality of axial ribs. In one or more embodiments, the outer sidewall 116 may have a plurality of radial ribs. In one or more embodiments, the outer sidewall 116 may have a grip surface for ease of manipulation by a practitioner. The grip surface may be textured or have a coating.

Figure 2A:
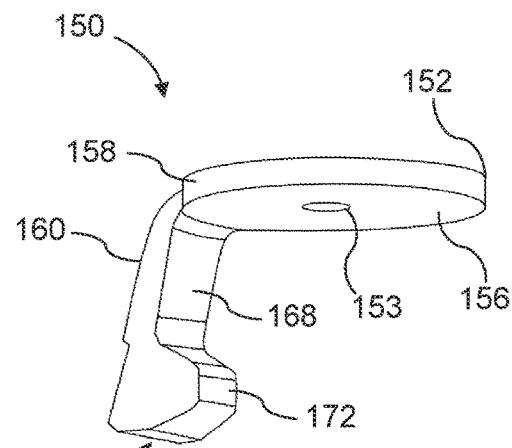
FIG. 2A illustrates a perspective view of an insert bottom view of the medical connector in accordance with the embodiment as shown in FIG. 1.
Figure 2B:
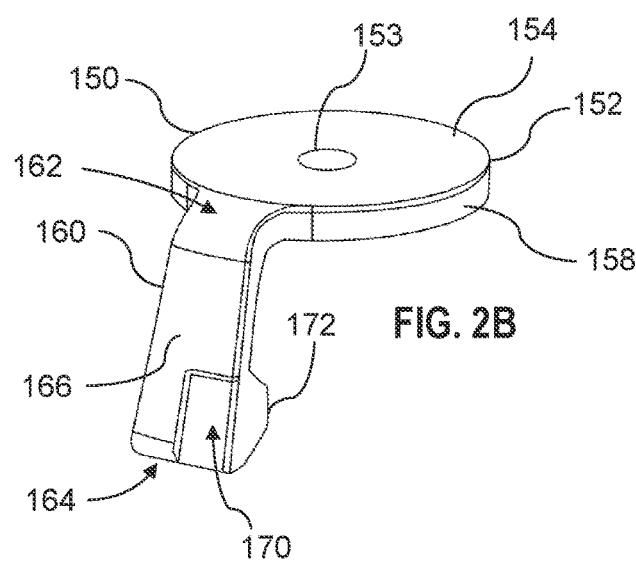
FIG. 2B illustrates a perspective view of an insert bottom view of the medical connector in accordance with the embodiment as shown in FIG. 1.

A second aspect of the present disclosure relates to an insert 150 disposed within the housing 110. As shown in FIGS. 2A and 2B, insert 150 has a generally discoid body 152 having a distal surface 154, a proximal surface 156 and a sidewall 158. From the sidewall 158 extends a locking tab 160, the locking tab 160 extending from the proximal surface 156 in a proximal direction away from the proximal surface 156 of the discoid body 152. In one or more embodiments, the discoid body 152 includes an aperture 153 disposed on the distal surface 154 of the discoid body 152, the aperture 153 extending therethrough. The center of the aperture 153 is concentric with the center of the discoid body 152. The discoid body 152 has a diameter $D_{DB}$, the diameter $D_{DB}$ being smaller than the diameter Dis of the partially cylindrical inner sidewall 120, defining a gap between the gap between the sidewall 158 and the partially cylindrical inner sidewall 120 of the housing 110.

In one or more embodiments, the locking tab 160 is a cantilevered prong having a distal portion 162 and a proximal portion 164. In one or more embodiments, the distal portion 162 is integral with the sidewall 158 of the discoid body 152. In one or more, the distal portion 162 and the sidewall 158 of the discoid body 152 can be bonded together through ultrasonic welding or solvent resistant biocompatible adhesive. In the preferred embodiment, the distal portion 162 is at an obtuse angle with respect to the proximal surface 156 of the discoid body 152. In one or more embodiments, the distal portion is at a right angle or at an acute angle with respect to the proximal surface 156 of the discoid body 152. In one or more embodiments, the locking tab 160, the distal portion 162 and the proximal portion bend deflect or elastically deform, either in combination or individually. In an exemplary implementation, at least a portion of the locking tab 160 elastically deforms inwardly to cause an interference fit between the locking tab 160 and the corresponding medical connector.

The proximal portion 164 of the locking tab 160 further comprises an outer wall 166 and an inner wall 168. The outer wall 166 of the locking tab 160 includes a recessed notch 170. The recessed notch 170 is adjacent to the proximal edge of proximal portion 164 and extends in a distal direction at least partially the length of the proximal portion 164. In one or more embodiments, the recessed notch 170 is adjacent to the lateral or right edge of the outer wall 166 with respect to the outer wall 166. In one or more embodiments, the recessed notch 170 is adjacent to the medial edge or left edge of the outer wall 166 with respect to the outer wall 166.

In one or more embodiments, where the corresponding medical connector is advanced distally into the housing 110 by threading the corresponding medical connector in a rightward or lateral angular direction as per ISO 80369-7: 2016 standards, the recessed notch 170 is disposed on the lateral or right edge of the outer wall 166 with respect to the outer wall 166. In one or more embodiments, where the corresponding medical connector is advanced distally into the housing 110 by threading the corresponding medical connector in a leftward angular direction, the recessed notch 170 is disposed on the medial or left edge of the outer wall 166 with respect to the outer wall 166. The depicted embodiment of FIGS. 2A and 2B show the recessed notch 170 disposed on the lateral or right edge of the outer wall 166 with respect to the outer wall 166. In one or more embodiment of the current disclosure, the recessed notch 170 is rectangular. In one or more alternate embodiments of the current disclosure, the recessed notch may also be semi-circular, semi-ovular, triangular, or any other geometric shape.

At least one thread 172 is disposed on the inner wall 168 of the locking tab 160. In the preferred embodiment, the at least one thread 172 has a helical shape. The helical shape is essentially tapered from one direction to another. In one or more embodiments, the taper decreases from a rightward or lateral direction to a medial or left direction with respect to the outer wall 166.

In one or more embodiments, where the corresponding medical connector is advanced distally into the housing 110 by threading the corresponding medical connector in a clockwise, rightward or lateral angular direction as per ISO 80369-7:2016 standards, the taper decreases from a clockwise direction with respect to the outer wall 166. In one or more embodiments, where the corresponding medical connector is advanced distally into the housing 110 by threading the corresponding medical connector in a counter-clockwise or leftward angular direction, the taper decreases from a counter-clockwise direction with respect to the outer wall 166. The depicted embodiment of FIGS. 2A and 2B show the taper decreasing from a clockwise direction with respect to the outer wall 166.

In one or more embodiments, the corresponding medical connector is first partially advanced distally into the housing 110 until a luer tip of the corresponding medical connector abuts the proximal surface 154 of the discoid body 152. In one or more embodiments, the corresponding medical connector is first partially advanced distally into the housing 110 until threads of the corresponding medical connector abut the at least one thread 172. In one or more embodiments, advancement of the corresponding medical connector into the housing 110 causes advancement of the discoid body 152 into the housing body 110. The corresponding medical connector can then be rotated which causes locking and final advancement of the discoid body 152 into the housing 110.

Figure 3:
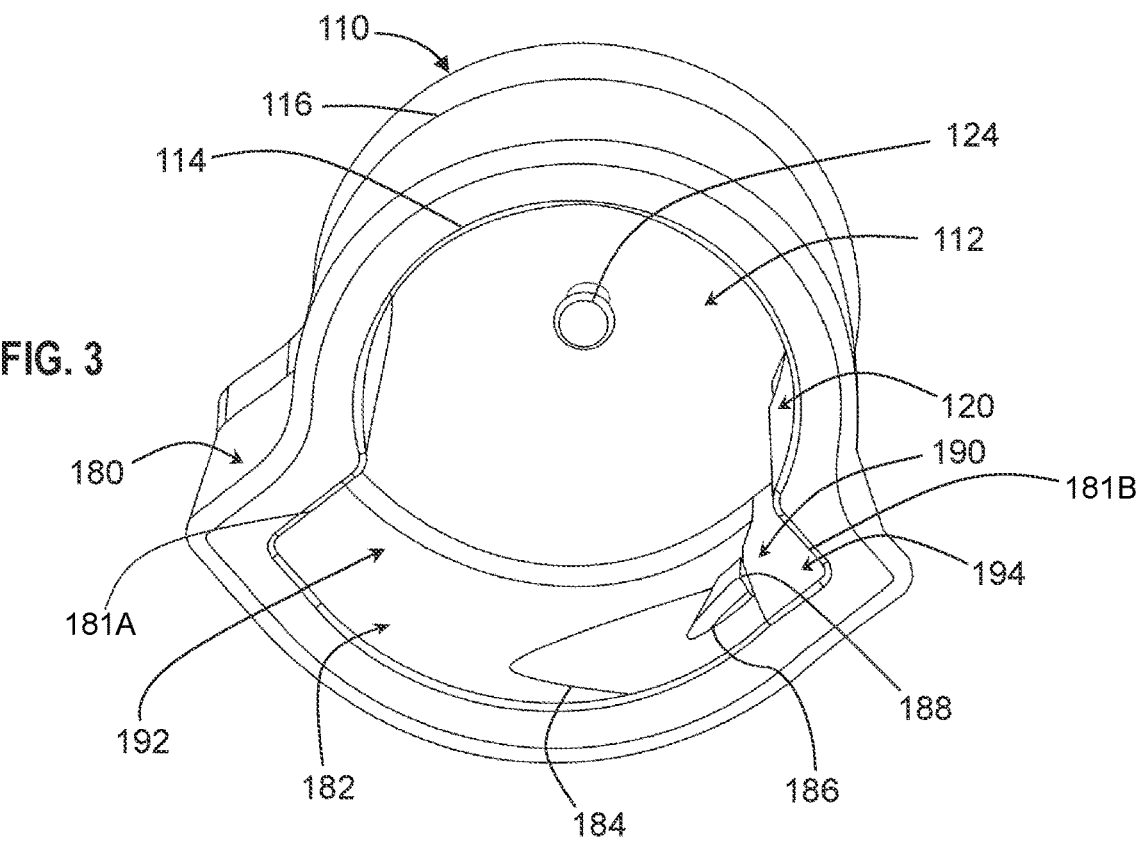
FIG. 3 illustrates a perspective bottom view of the housing body of the medical connector in accordance with the embodiment as shown in FIG. 1.

A third aspect of the present disclosure, as shown in FIG. 3, relates to the locking structure disposed within the cavity 130 of housing 110, the locking structure having features which are disposed or integral with the radial sidewall 182 of the housing 110. The locking structure includes an outwardly sloped surface 184 which slopes outwardly counter-clockwise from a first sidewall 181A to a second sidewall 181B. In the depicted embodiment, the outwardly sloped surface 184 extends at least partially the length of the arc of the radial sidewall 182. In one or more embodiments, the outwardly sloped surface 184 extends the entire length of the arc of the radial sidewall 182. From a lateral portion of the outwardly sloped surface 184 extends a sloped tab 186. The sloped tab 186 slopes outwardly clockwise. The sloped tab 186 includes a ledge 188 formed by a wall at a substantially right angle with respect to the radial sidewall 182. In one or more embodiments, adjacent to the ledge 188 is a proximally sloped surface 190, the proximally sloped surface 190 slopes inwardly with respect to the radial sidewall 182 from a distal position to a proximal position.

Figure 4:
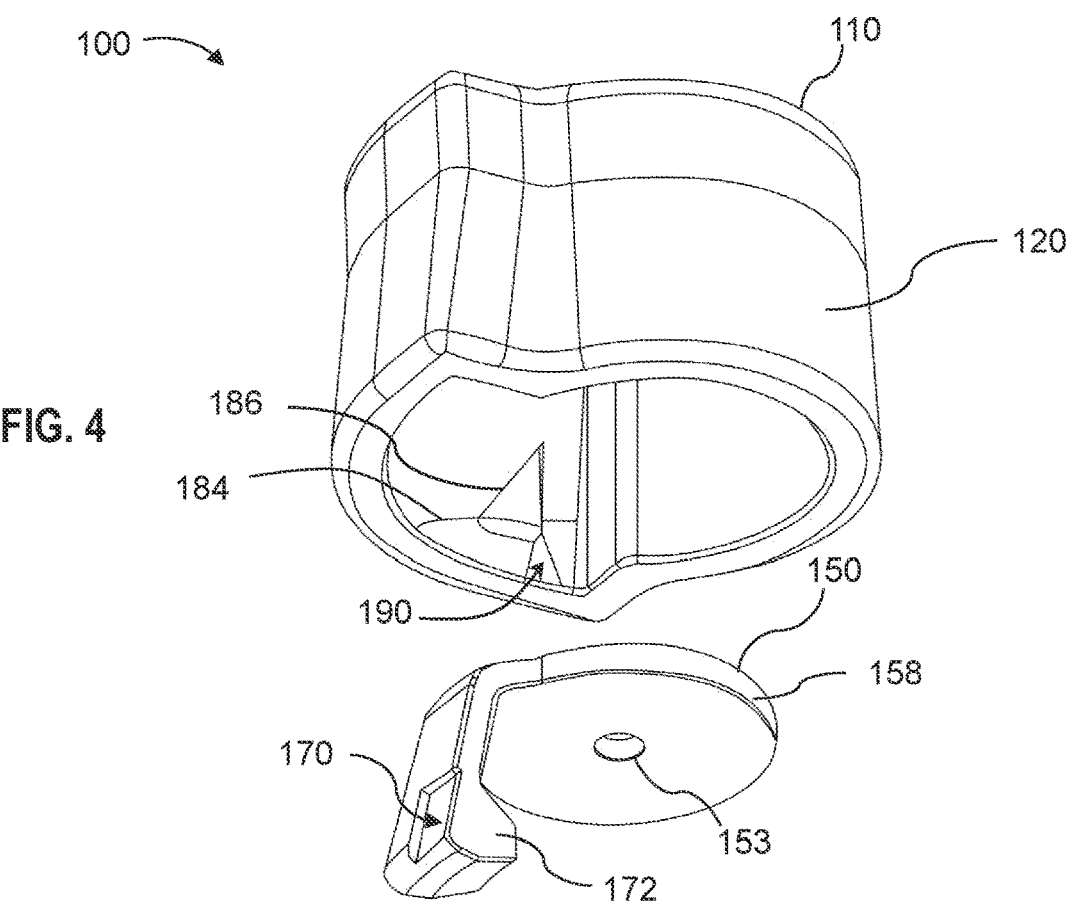
FIG. 4 illustrates a perspective side view of the housing body and the insert of the medical connector in accordance with the embodiment as shown in FIG. 1.

As shown in FIG. 3, a portion of the radial sidewall 182 adjacent to the first sidewall 181A is substantially smooth with no protrusions or indentations, and portion of the radial sidewall 182 adjacent to the second sidewall 181B includes the outwardly sloped surface 184, sloped tab 186, the ledge 188 and the proximally sloped surface 190. As used herein, a first position 192 is defined by the portion of the radial sidewall 182 adjacent to the first sidewall 181A and a locking position 194 is defined by the sloped tab 186 and the ledge 188. As shown in FIG. 4, when insert 150 is advanced distally into the cavity 130 of the housing 110, the locking tab 160 is disposed in the first position 192. In one or more embodiments, advancement of the insert 150 into the cavity 130 causes the locking tab to elastically deform outwardly with respect to the radial sidewall 182. With the insert 150 fully advanced into the cavity 130, the insert 150 can rotate freely along the arc of the radial sidewall 182. As the insert 150 approaches the locking position 194, the outwardly sloped surface 184 further elastically deforms the locking tab 160 until the recessed notch 170 passes the ledge 188 of the radial sidewall 182. When the notch 170 has passed the ledge 188, the notch nonreleasably engages the ledge 188, thereby preventing clockwise movement of the locking tab 160.

In some embodiments, when the notch 170 has passed the ledge 188, an audible click or sound is created and is detectable by the clinician or ancillary detection systems to indicate that the insert 150 and thus the needleless connector has reached a fully locked position.

Figure 5:
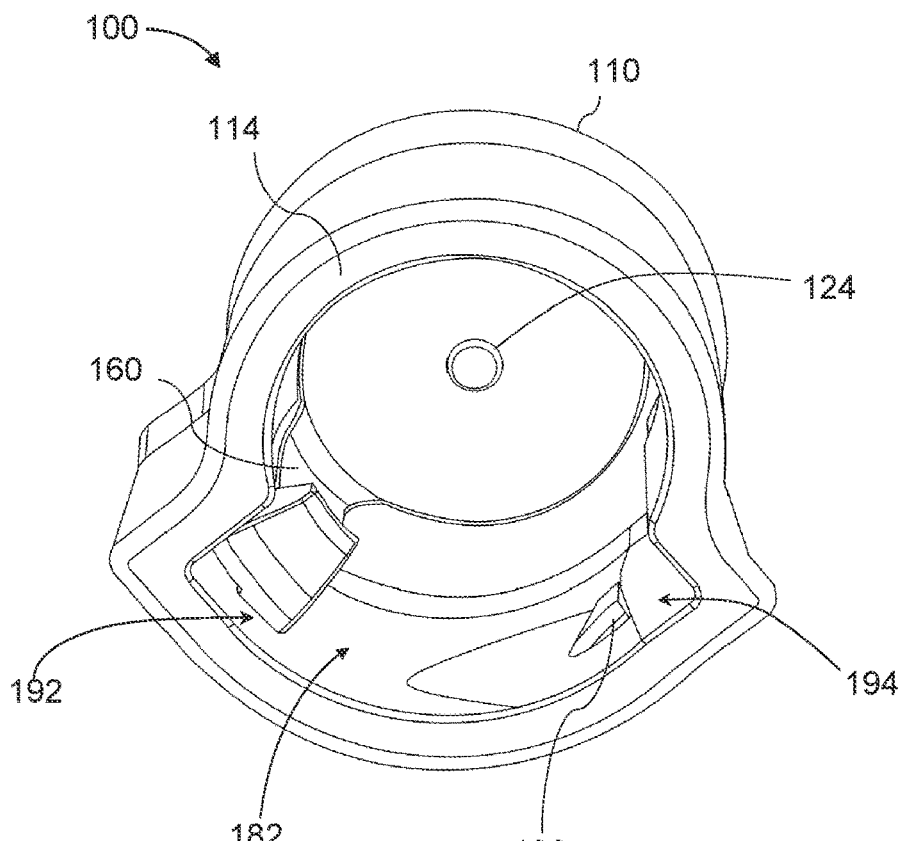
FIG. 5 illustrates a perspective bottom view of the housing body of the medical connector in accordance with the embodiment as shown in FIG. 1.
Figure 6:
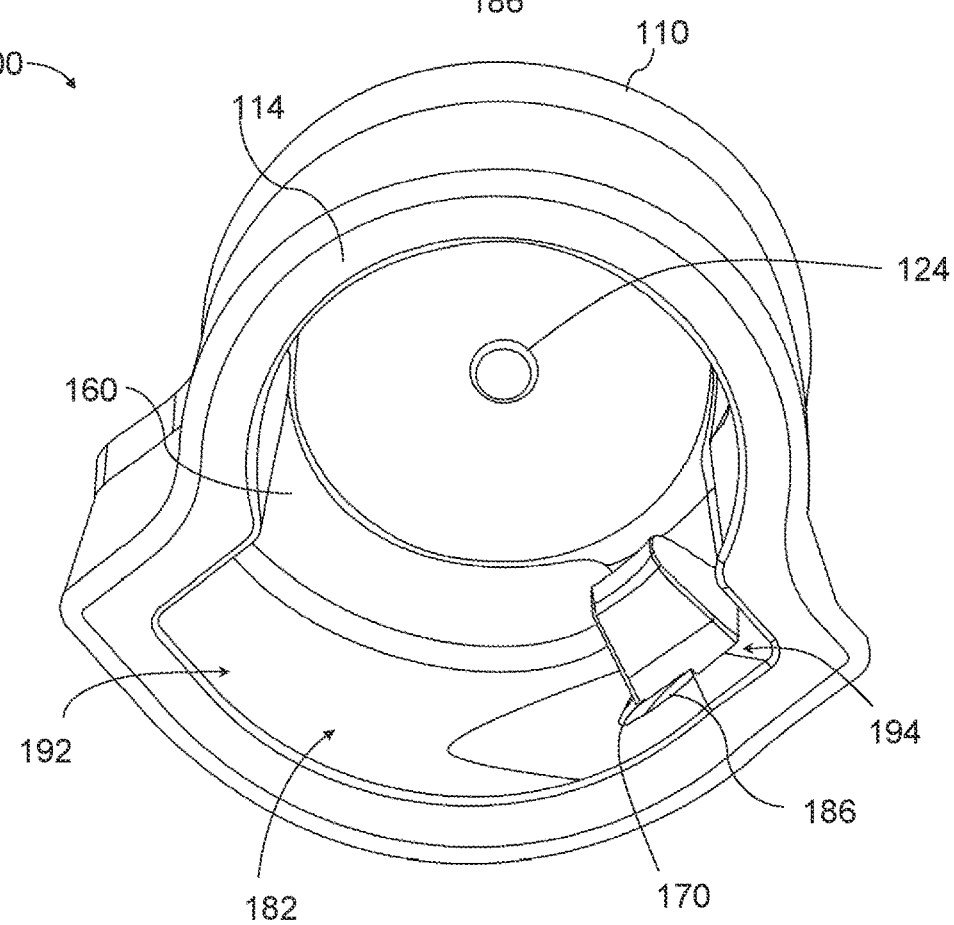
FIG. 6 illustrates a perspective bottom view of the housing body and the insert of the medical connector in accordance with the embodiment as shown in FIG. 1.
Figure 7:
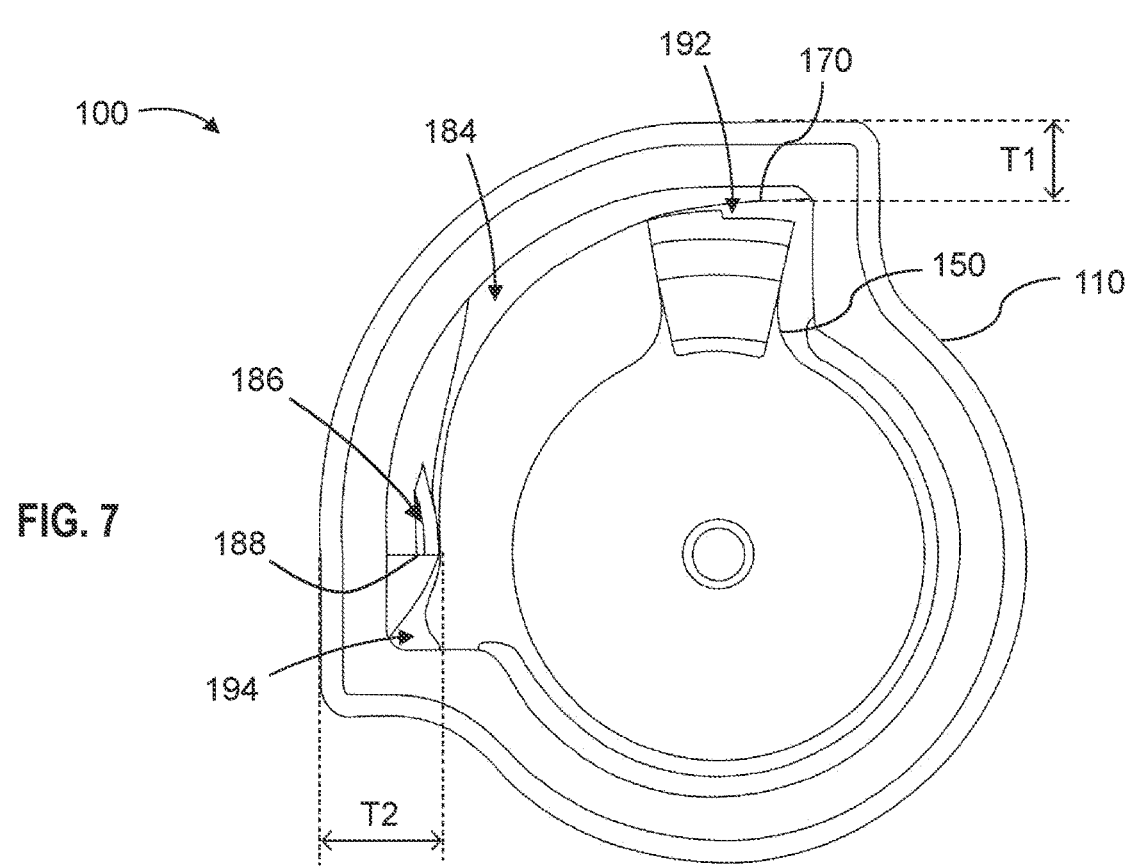
FIG. 7 illustrates a bottom view of the housing body and the insert of the medical connector in accordance with the embodiment as shown in FIG. 1.
Figure 8:
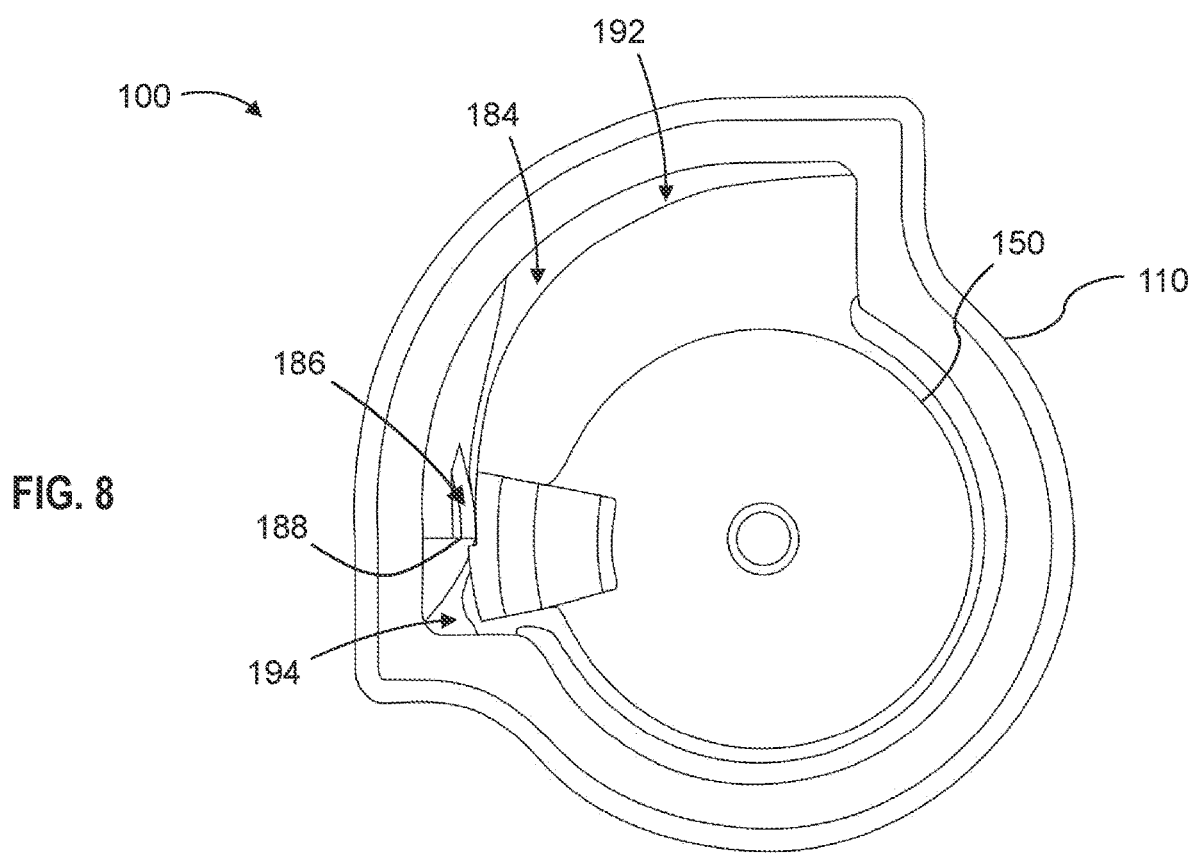
FIG. 8 illustrates a bottom view of the housing body and the insert of the medical connector in accordance with the embodiment as shown in FIG. 1.

FIGS. 5 and 6 illustrate perspective views of the insert 150 in the first position 192 and the locking position 194, respectively. Likewise, FIGS. 7 and 8 illustrate a top view of the insert 150 in the first position 192 and the locking position 194, respectively. As depicted in FIGS. 7 and 8, the thickness of the radial sidewall 182 gradually increases from a value of $T_1$ to $T_2$ due to the outwardly sloped surface 184.

Figure 9:
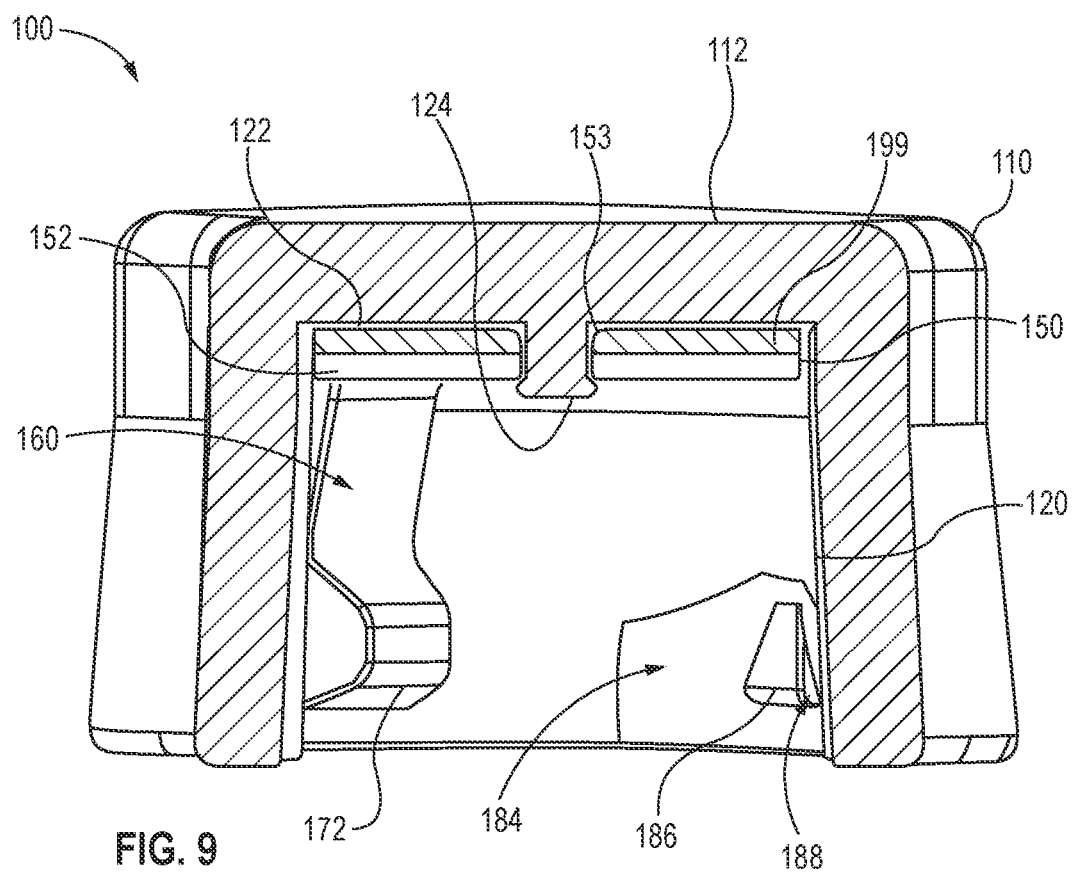
FIG. 9 illustrates a cross-sectional side view of the housing body and the insert of the medical connector in accordance with the embodiment as shown in FIG. 1.

FIG. 9 depicts a partially cross-sectional view of the cavity 130 wherein the insert 150 is fully advanced into the cavity 130 and is in the first position 192. For illustration purposes, the distal surface 154 of the discoid body 152 directly abuts the inner top surface 122 of the housing 110, however, in one or more embodiments, an absorbent material 199 containing disinfectant is disposed between the distal surface 154 of the discoid body 152 and the inner top surface 122 of the housing 110. Advancement of a corresponding medical connector into cavity 130 compresses the absorbent material 199 thereby releasing disinfectant. In one or more embodiments, the closed end 112 includes a concentric retention tab 124 which mechanically locks onto the aperture 153 of the discoid body 152, thereby preventing removal of the insert 150. In one or more embodiments, the concentric retention tab comprises a distal cylindrical shape and a proximal cylindrical shape, the proximal cylindrical shape having a greater diameter than the distal cylindrical shape. In one or more embodiments, the diameter of the proximal cylindrical shape is greater than the diameter of the aperture 153 of the discoid body 152, creating a snap-fit connection between the retention tab 124 and the aperture 153 of the discoid body 152.

In one or more embodiments, the retention tab 124 is long enough to allow for placement of a cylindrical absorbent material disk between the discoid body 152 and the inner top surface 122 of the housing 110, the cylindrical absorbent material disk having an aperture extending therethrough. The total length of the retention tab 124 is equal or slightly greater than the thickness of the discoid body 152 and the thickness of the cylindrical absorbent material disk, whereby the cylindrical absorbent material disk is in an uncompressed state. Insertion of a connector compresses the cylindrical absorbent material disk, thereby releasing disinfectant into the cavity 130.

Figure 11:
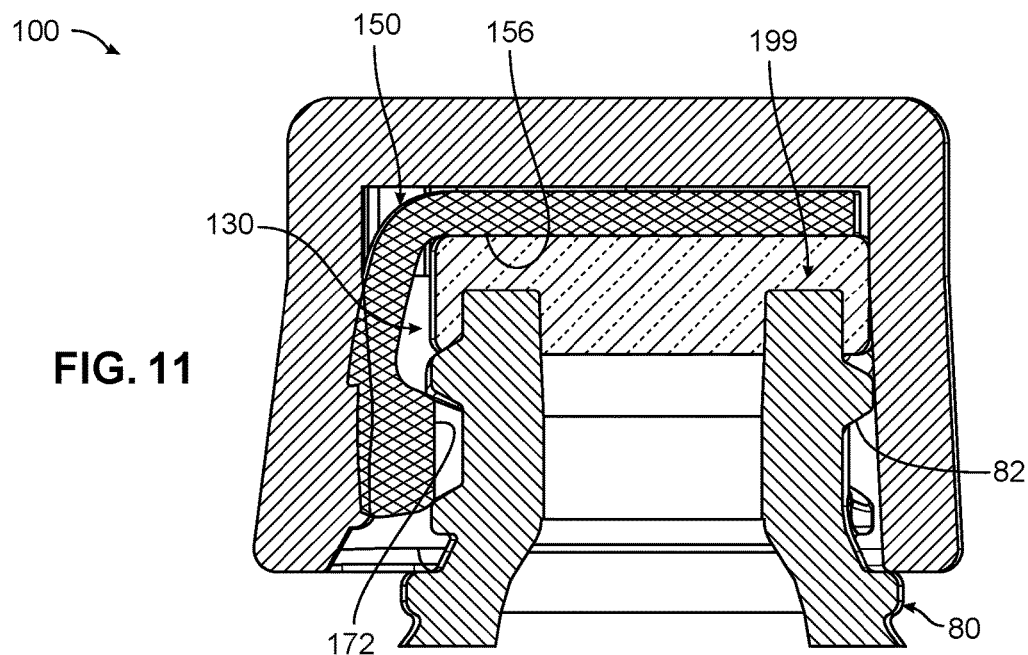
FIG. 11 illustrates a cross-sectional view of a medical connector inserted in the housing body and the insert of the medical connector.
Figure 12:
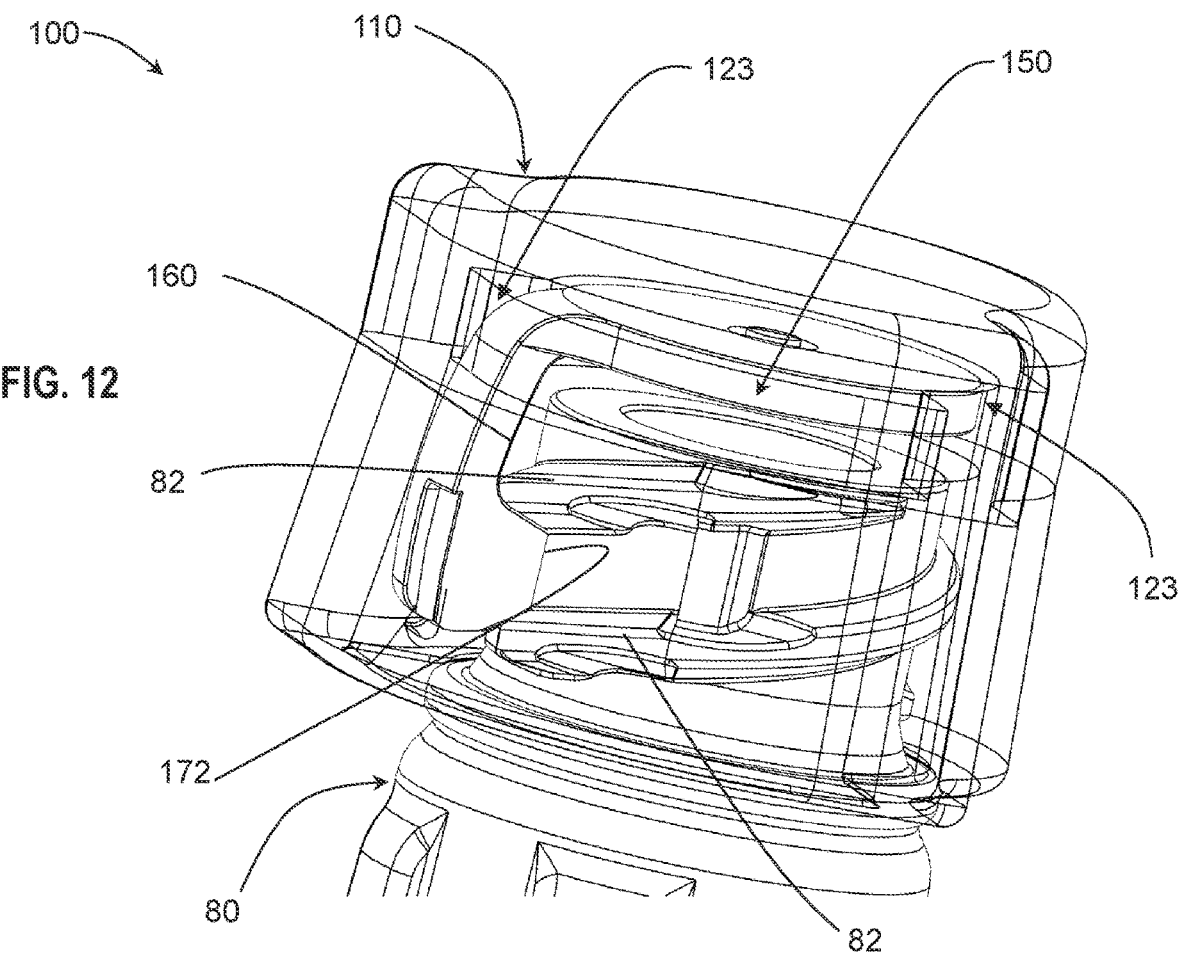
FIG. 12 illustrates a side perspective view of the medical connector inserted in the housing body and the insert of the medical connector.

As shown in FIGS. 11 and 12, the corresponding medical connector is a female needleless connector 80.

As shown in FIG. 11, in one or more embodiments, the absorbent material 199 is placed in the cavity 130, the absorbent material 199 abutting the proximal surface 156 of the discoid body 152. Insertion of a female needleless connector 80 compresses the absorbent material 199, thereby releasing disinfectant into the cavity 130. At least one thread 82 of the connector 80 engages at the at least one thread 172 of the insert 150. The at least one thread 82 is disposed on a hub 84 of the female needleless connector 80.

Figure 10:
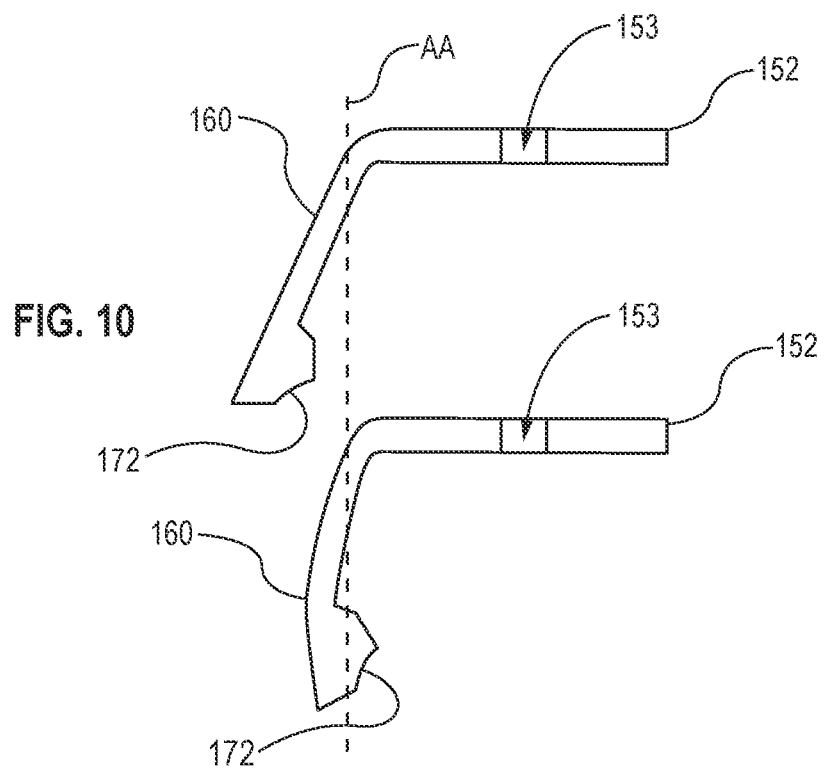
FIG. 10 illustrates the elastic deformation of the locking tab in the first position and the locking position.

As shown in FIG. 12, in operation, a female connector 80 having at least one thread 82 engages the at least one thread 172 of the insert 150, thereby causing advancement of the female connector 80 and the insert 150 into the housing 110. As the locking tab 160 nonreleasably locks into the second position and the absorbent material 199 (not shown for purposes of clarity) is compressed, disinfectant is released into the cavity 130. In embodiments where the absorbent material 199 is disposed against the closed distal end 112 of the housing 110, the released disinfectant evacuates through the gap 123 created between the discoid body 152 and the partially cylindrical inner sidewall 120. After disinfection is complete, the female connector 80 is un-threaded in the opposite direction, allowing for release of the female connector 80 while the ledge 188, engaged to the recessed notch 170, prevents the removal of the insert 150. FIG. 10 depicts the elastic deformation of the locking tab 160 in the first position 192 and the locking position 194, respectively. The deformation causes the at least one thread 172 to further securely engage the at least one thread of the female connector 80. For purposes of illustration, the locking tab 160 in the first position 192 is depicted directly above the locking tab 160 in the locking position. Deformation of the locking tab 160 is illustrated relative to the line AA, with the locking tab 160 deforming inward.

A second embodiment of the present disclosure relates to a housing 210 of syringe 200. As shown in FIGS. 13A through 13D, the housing 210 protrudes in a distal direction from a distal wall 212 of a syringe barrel 213 of the syringe 200. As shown in 13A, the housing 210 of the second embodiment is configured as a needleless connector able to receive a male luer fitting commonly associated with VADs. The housing 210 includes a cavity 230 defined by the distal wall 212 of the syringe barrel 213, an open end 214 opposite the distal wall 212 and a partially cylindrical sidewall 216 extending from the distal wall 212 to the open end 214. A tapered hub 232 is disposed within the cavity 230, the tapered hub 232 extending in a distal direction from the distal wall 212 of the syringe barrel 213. The tapered hub 232 is configured to interdigitate with a corresponding cavity of a housing of the VAD (not shown). In some embodiments, the tapered hub 232 is configured to create a fluid-tight seal with the housing of the VAD. In some embodiments, the tapered hub 232 is configured to create an interference fit with the housing of the VAD.

The housing 210 and the partially cylindrical sidewall 216 are of a partially cylindrical shape, the partially cylindrical sidewall 216 having an integral radial protrusion 280 extending laterally from the housing 210. The radial protrusion 280 defines a radial sidewall 282, the radial sidewall 282 including a locking structure described in further detail below. The radial protrusion 280 and the radial sidewall 282 are in the shape of a laterally protruding arc. The angle of the protruding arc ranges from 10 degrees to 350 degrees.

In one or more embodiments, the partially cylindrical inner sidewall 216 has a substantially constant diameter. In one or more embodiments, the partially cylindrical inner sidewall 216 can include an outward taper, wherein the taper increases distally towards the open end 214.

The housing 210 further includes an outer sidewall 216. The outer sidewall 216 in the depicted embodiment has partially cylindrical shape which includes a smooth surface and a chamfer 218. In one or more embodiments, the chamfer 218 may be rounded. In one or more embodiments the chamfer 218 may extend partially around the distal end of the outer sidewall 216.

Figure 13A:
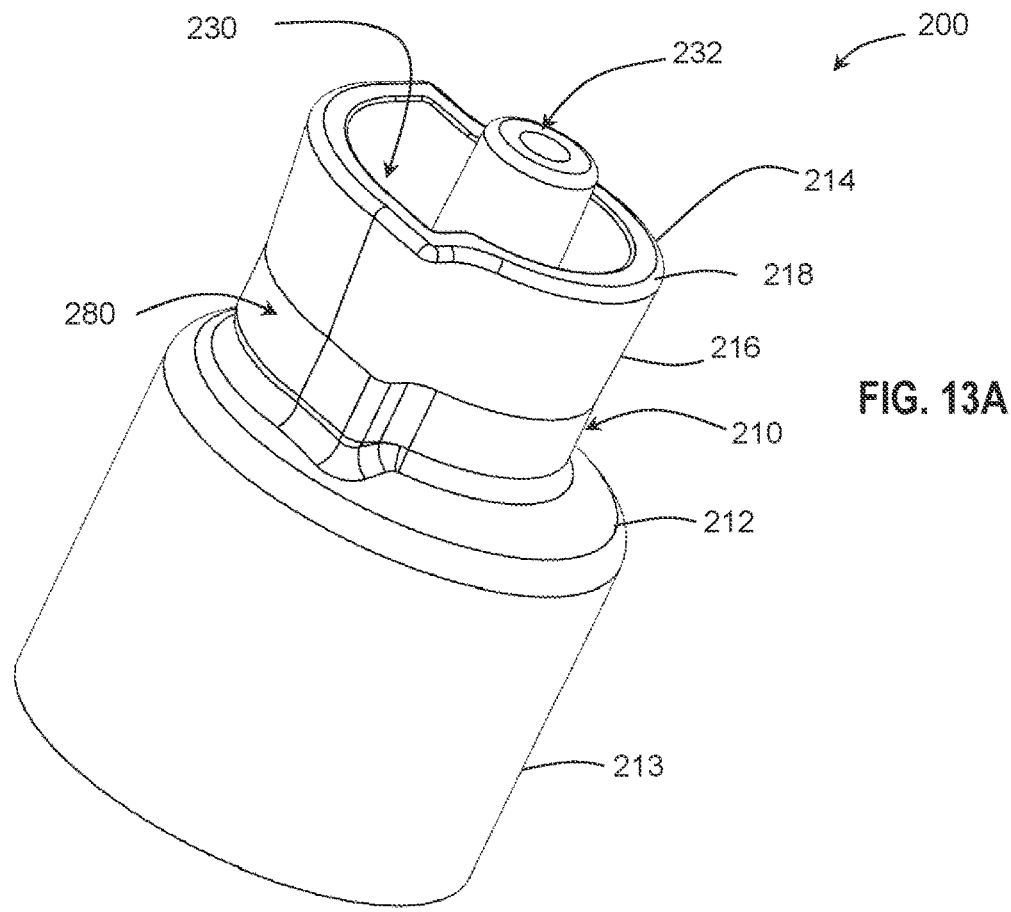
FIG. 13A illustrates a perspective view of a housing of a syringe in accordance with a second embodiment of the present disclosure.
Figure 13B:
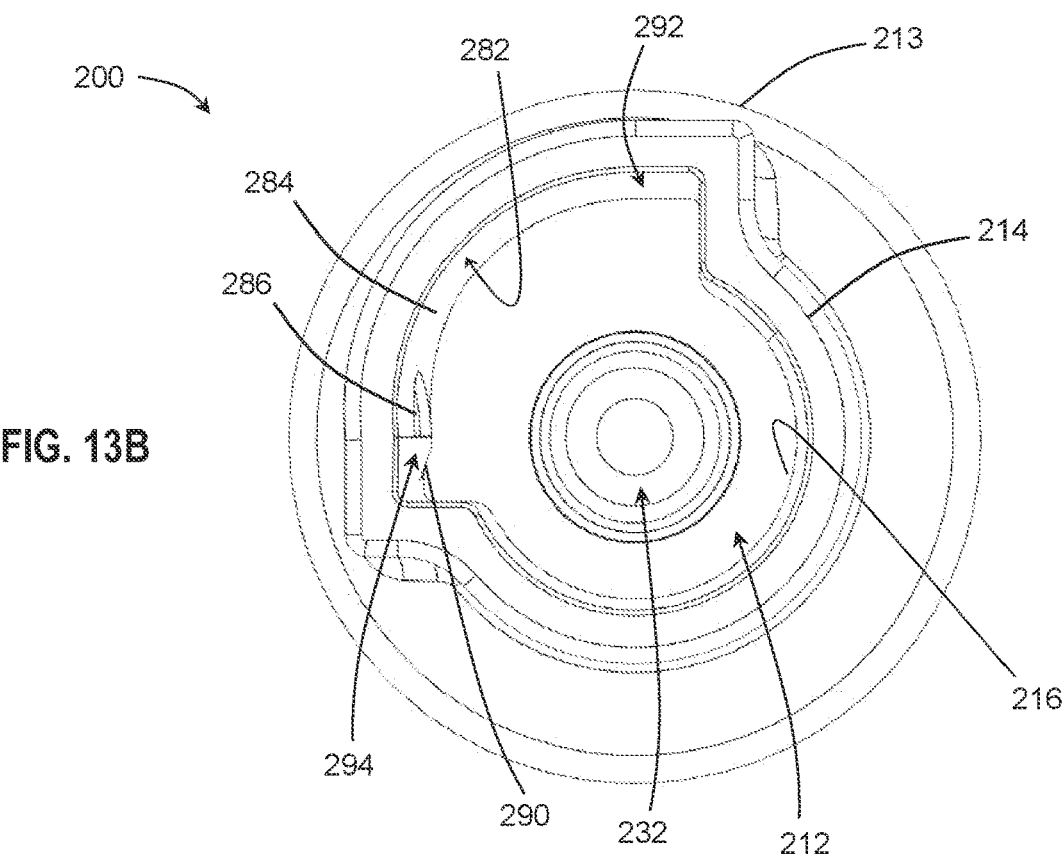
FIG. 13B illustrates a top view of the housing of the syringe in accordance with the second embodiment as shown in FIG. 13A.

The locking structure, as best shown in FIGS. 13B though 13D, is disposed within the cavity 230 of housing 210, the locking structure having features which are integral with the radial sidewall 282 of the housing 210. The locking structure includes an outwardly sloped surface 284 which slopes outwardly from a medial or leftward position to a lateral or rightward position. In the depicted embodiment, the outwardly sloped surface 284 extends at least partially the length of the arc of the radial sidewall 282. In one or more embodiments, the outwardly sloped surface 284 extends the entire length of the arc of the radial sidewall 282. From a lateral portion of the outwardly sloped surface 284 extends a sloped tab 286. The sloped tab 286 slopes outwardly from a lateral or rightward position to a medial or leftward position. The sloped tab 286 includes a ledge 288 formed by a wall at a substantially right angle with respect to the radial sidewall 282. In one or more embodiments, adjacent to the ledge 288 is a proximally sloped surface 290, the proximally sloped surface 290 slopes inwardly with respect to the radial sidewall 282 from a distal position to a proximal position.

Figure 13C:
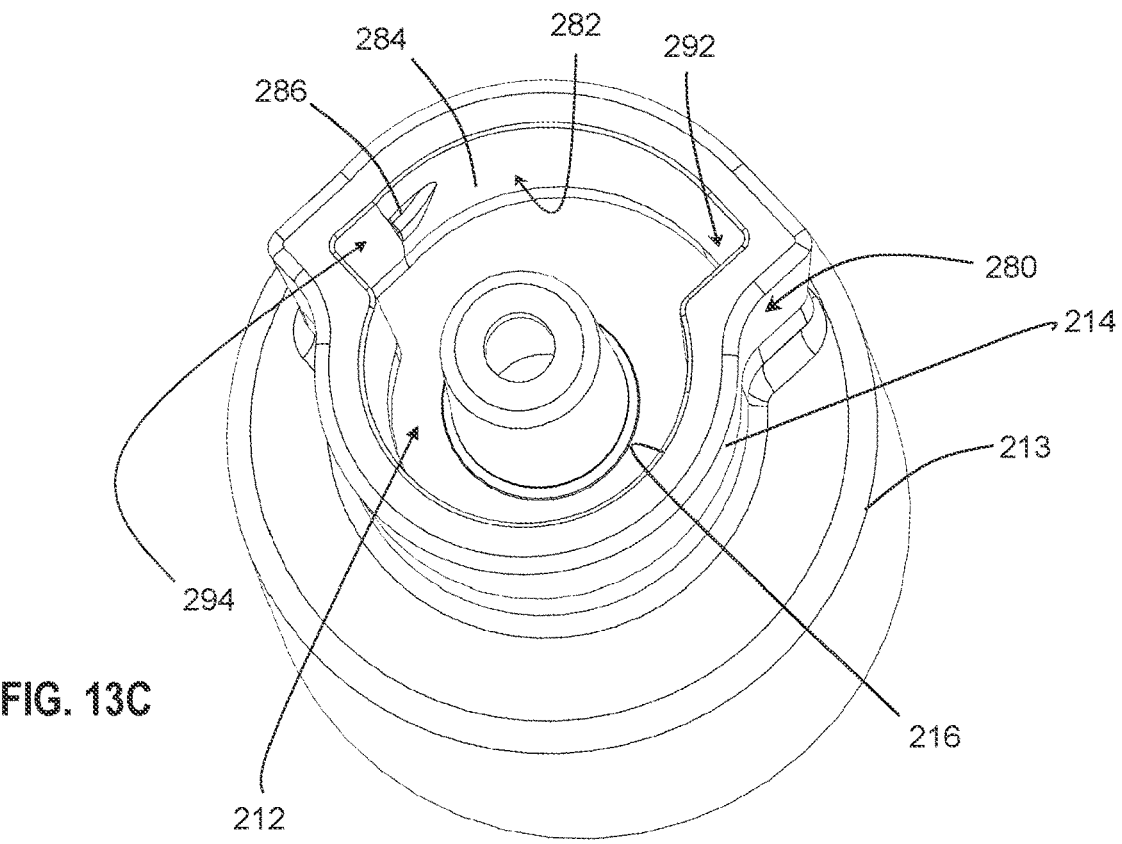
FIG. 13C illustrates a perspective side view of the housing of the syringe in accordance with the second embodiment as shown in FIG. 13A.
Figure 13D:
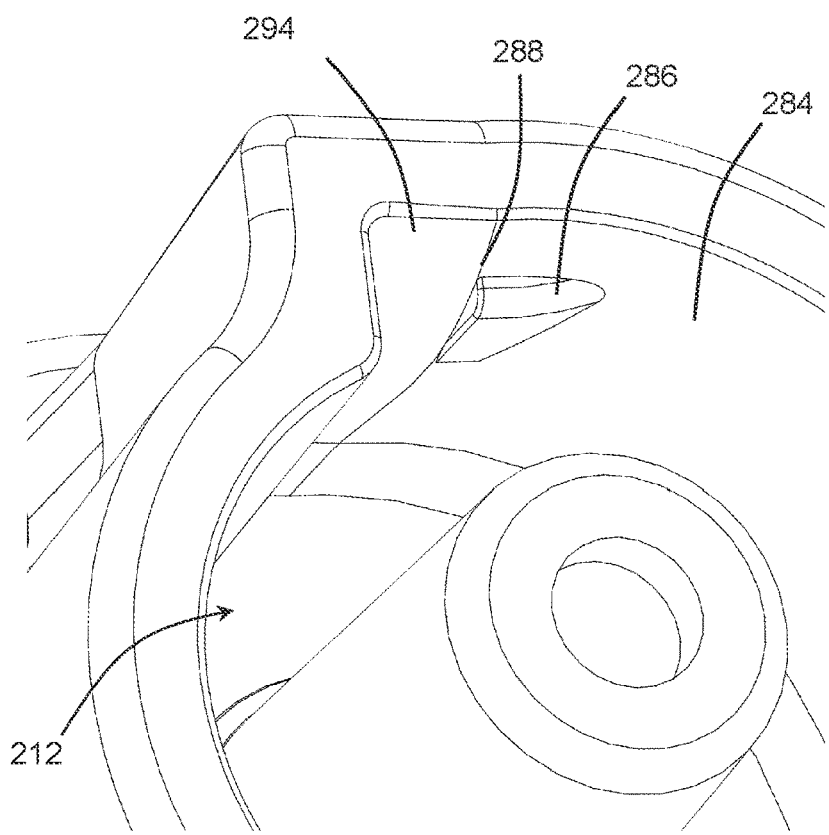
FIG. 13D illustrates a perspective side view of the housing of the syringe in accordance with the second embodiment as shown in FIG. 13A.

As best shown in FIGS. 13C and 13D, a medial or leftward portion of the radial sidewall 282 is substantially smooth with no protrusions or indentations, and a lateral or rightward portion of the radial sidewall 282 includes the outwardly sloped surface 284, sloped tab 286, the ledge 288 and the proximally sloped surface 290. As used herein, a first position 292 is defined by the medial or leftward portion of the radial sidewall 282 and a locking position 294 is defined by the sloped tab 286 and the ledge 288.

Figure 14A:
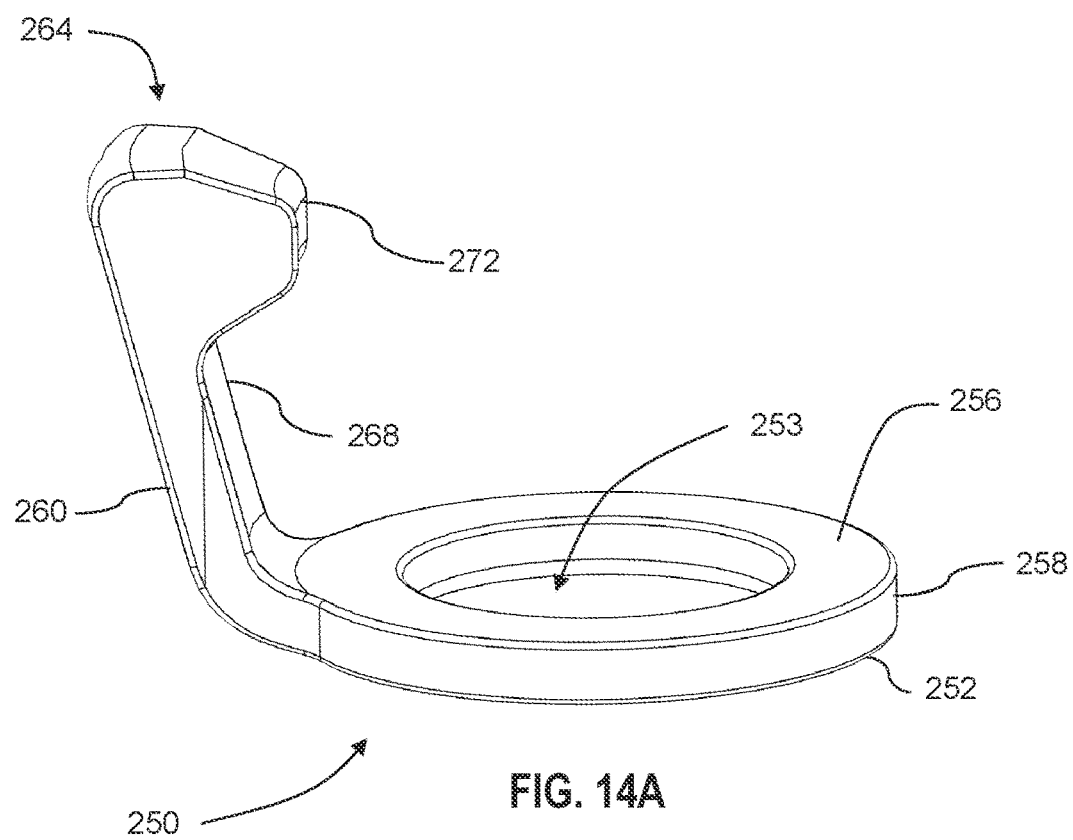
FIG. 14A illustrates a perspective side view of an insert in accordance with the second embodiment as shown in FIG. 13A.
Figure 14B:
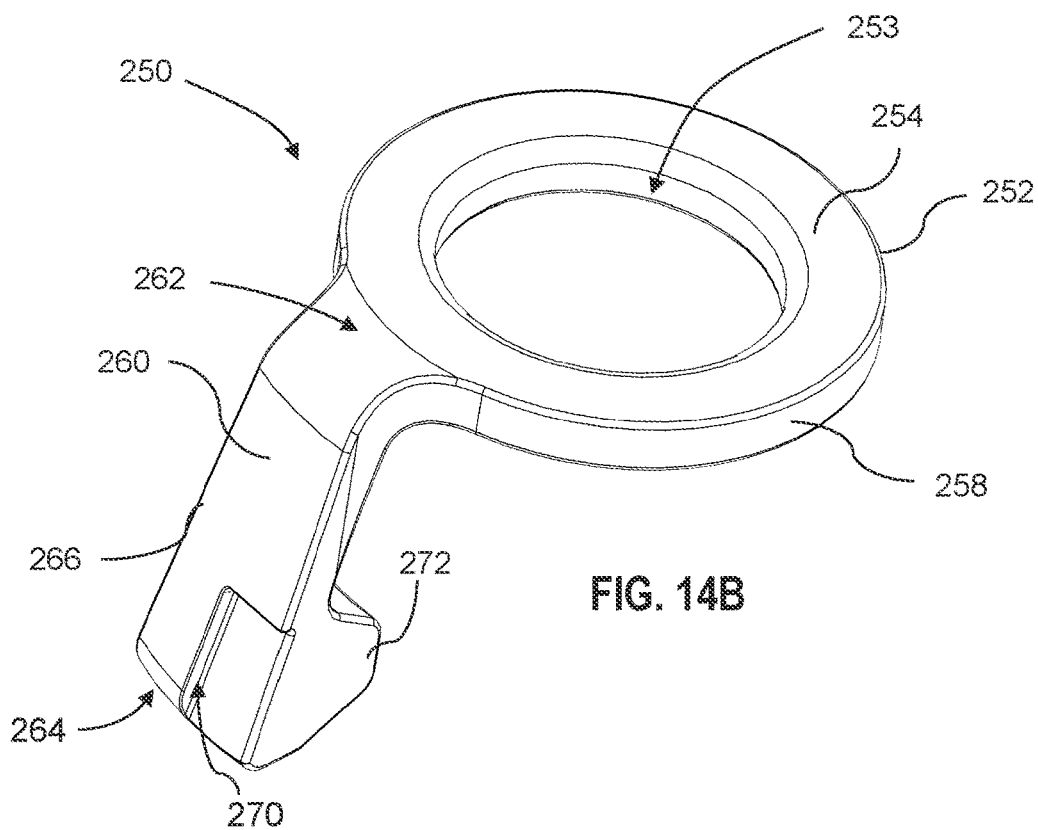
FIG. 14B illustrates a perspective side view of the insert in accordance with the second embodiment as shown in FIG. 13A.

As shown in FIGS. 14A and 14B, insert 250 has a generally discoid body 252 having a proximal surface 254, a distal surface 256 and a sidewall 258. From the sidewall 258 extends a locking tab 260, the locking tab 260 extending from the distal surface 256 in a distal direction away from the distal surface 256 of the discoid body 252. In one or more embodiments, the discoid body 252 includes an aperture 253 disposed on the proximal surface 254 of the discoid body 252, the aperture 253 extending therethrough. The center of the aperture 253 is concentric with the center of the discoid body 252. The discoid body 252 has a diameter $D_{DB}$, the diameter $D_{DB}$ being smaller than the diameter Dis of the partially cylindrical inner sidewall 220, defining a gap between the gap between the sidewall 258 and the partially cylindrical inner sidewall 220 of the housing 210.

In one or more embodiments, the locking tab 260 is configured as a cantilevered prong having a proximal portion 262 and a distal portion 264. In one or more embodiments, the proximal portion 262 is integral with the sidewall 258 of the discoid body 252. In one or more, the proximal portion 262 and the sidewall 258 of the discoid body 252 can be bonded together through ultrasonic welding or solvent resistant biocompatible adhesive. In the preferred embodiment, the proximal portion 262 is at an obtuse angle with respect to the distal surface 256 of the discoid body 252. In one or more embodiments, the proximal portion 262 is at a right angle or at an acute angle with respect to the distal surface 256 of the discoid body 252. In one or more embodiments, the locking tab 260, the proximal portion 262 and the distal portion bend deflect or elastically deform, either in combination or individually. In an exemplary implementation, at least a portion of the locking tab 260 elastically deforms inwardly to cause an interference fit between the locking tab 260 and the corresponding medical connector.

The proximal portion 264 of the locking tab 260 further comprises an outer wall 266 and an inner wall 268. The outer wall 266 of the locking tab 260 includes a recessed notch 270. The recessed notch 270 is adjacent to the distal edge of the distal portion 264 and extends in a proximal direction at least partially the length of the distal portion 264. In one or more embodiments, the recessed notch 270 is adjacent to the lateral or right edge of the outer wall 266 with respect to the outer wall 266. In one or more embodiments, the recessed notch 270 is adjacent to the medial edge or left edge of the outer wall 266 with respect to the outer wall 266.

Figure 15:
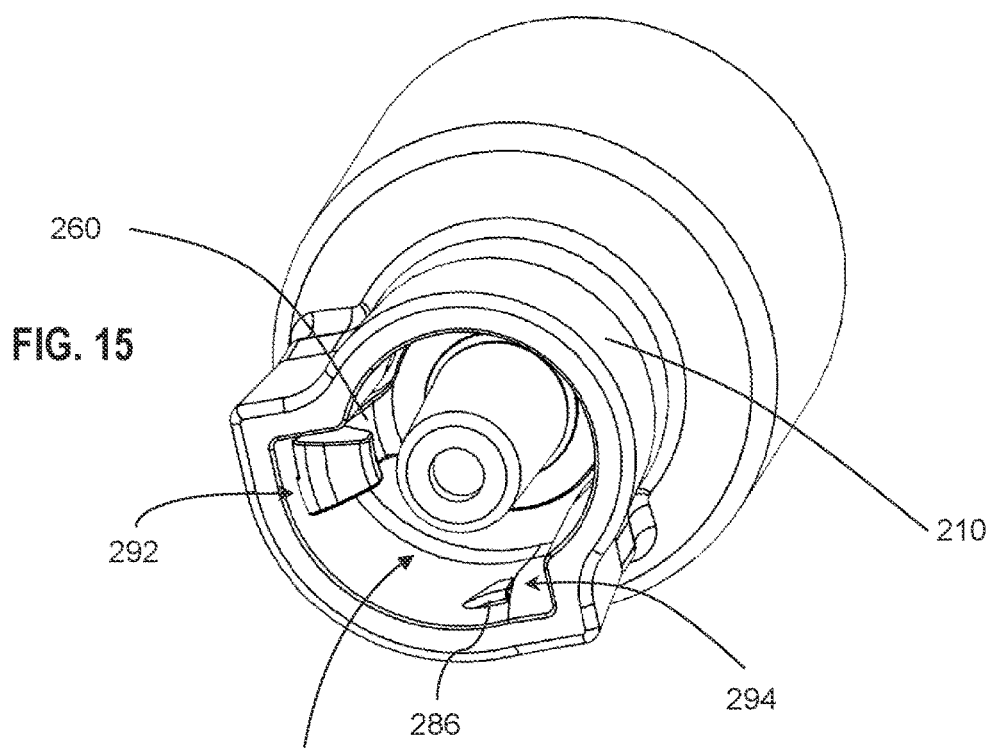
FIG. 15 illustrates a perspective side view of the insert inserted into the housing of the syringe in accordance with the second embodiment as shown in FIG. 13A.
Figure 16:
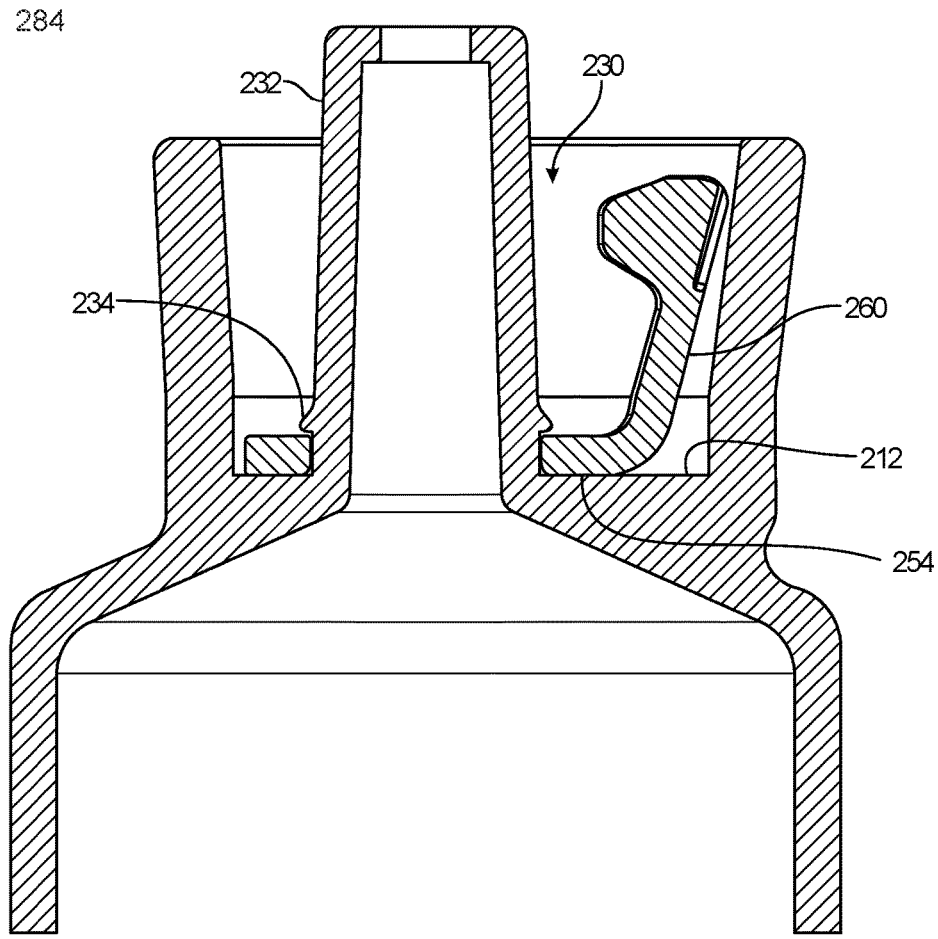
FIG. 16 illustrates a cross-sectional view of the insert inserted into the housing of the syringe in accordance with the second embodiment as shown in FIG. 13A.

As shown in FIGS. 15 and 16, in one or more embodiments, where the VAD is advanced proximally into the housing 210 by threading the VAD in a leftward angular direction as per ISO 80369-7:2016 standards, the recessed notch 270 is disposed on the medial or left edge of the outer wall 266 with respect to the outer wall 266. In one or more embodiments, where the VAD is advanced distally into the housing 210 by threading the VAD in a rightward angular direction, the recessed notch 270 is disposed on the medial or left edge of the outer wall 266 with respect to the outer wall 266. Referring back to the depicted embodiment of FIGS. 14A and 14B show the recessed notch 270 disposed on the lateral or right edge of the outer wall 266 with respect to the outer wall 266. In one or more embodiment of the current disclosure, the recessed notch 270 is rectangular. In one or more alternate embodiments of the current disclosure, the recessed notch 270 may also be semi-circular, semi-ovular, triangular, or any other geometric shape.

At least one thread 272 is disposed on the inner wall 268 of the locking tab 260. In the preferred embodiment, the at least one thread 272 has a helical shape. The helical shape is essentially tapered from one direction to another. In one or more embodiments, the taper decreases from a rightward or lateral direction to a medial or left direction with respect to the outer wall 266.

In one or more embodiments, where the VAD is advanced distally into the housing 210 by threading the VAD clockwise, rightward or lateral angular direction as per ISO 80369-7:2016 standards, the taper decreases from a leftward or medial direction with respect to the outer wall 266. In one or more embodiments, where the VAD is advanced proximally into the housing 210 by threading the VAD connector in a counter-clockwise or leftward angular direction, the taper decreases from a rightward or lateral direction with respect to the outer wall 266. The depicted embodiment of FIGS. 14A and 14B show the taper decreasing from a leftward or medial direction with respect to the outer wall 266.

As previously described with respect to the first embodiment, and as shown in FIGS. 15 and 16, when insert 250 is advanced proximally into the cavity 230 of the housing 210, the locking tab 260 is disposed in the first position 292. In one or more embodiments, advancement of the insert 250 into the cavity 230 causes the locking tab to elastically deform outwardly with respect to the radial sidewall 282. With the insert 250 fully advanced into the cavity 230, the insert 250 can rotate freely along the arc of the radial sidewall 282. As the insert 250 rotationally approaches the locking position 294, the outwardly sloped surface 284 further elastically deforms the locking tab 260 inward until the recessed notch 270 passes the ledge 288 of the radial sidewall 282. When the notch 270 has passed the ledge 288, the notch non-releasably engages the ledge 288, thereby preventing medial or leftward movement of the locking tab 260.

In some embodiments, when the notch 270 has passed the ledge 288, an audible click or sound is created and is detectable by the clinician or ancillary detection systems to indicate that the insert 250 and thus the medical connector has reached a fully locked position.

As best shown in FIG. 16, the proximal surface 254 of the insert 250 abuts the distal wall 212 of a syringe barrel 213 of the syringe 200 in the fully advanced position. In one or more embodiments, a circular protrusion 234 is disposed on the tapered hub 232. The circular protrusion 234 is configured to non-removably lock the insert 250 in the fully advanced position. The circular protrusion 234 is located a distance from the distal wall 212 of a syringe barrel 213 and the distance is configured to be equal to or slightly larger than the thickness of the discoid body of the insert 250. In one or more embodiments, the circular protrusion 234 has a substantially triangular cross section, the triangular cross section having a proximal right angled surface with respect to the tapered hub 232 and a distal acute angled surface with the tapered hub 232. The distal acute angled surface of the circular protrusion 234 is configured to create slight deformation of the insert 250 as the insert 250 comes into contact with the distal acute angled surface of the circular protrusion 234 as the insert 250 is advanced proximally. The proximal right surface of the circular protrusion 234 is configured to non-removably secure the insert 250 when the insert 250 completely transverses over the triangular cross section of the circular protrusion 234.

Figure 18B:
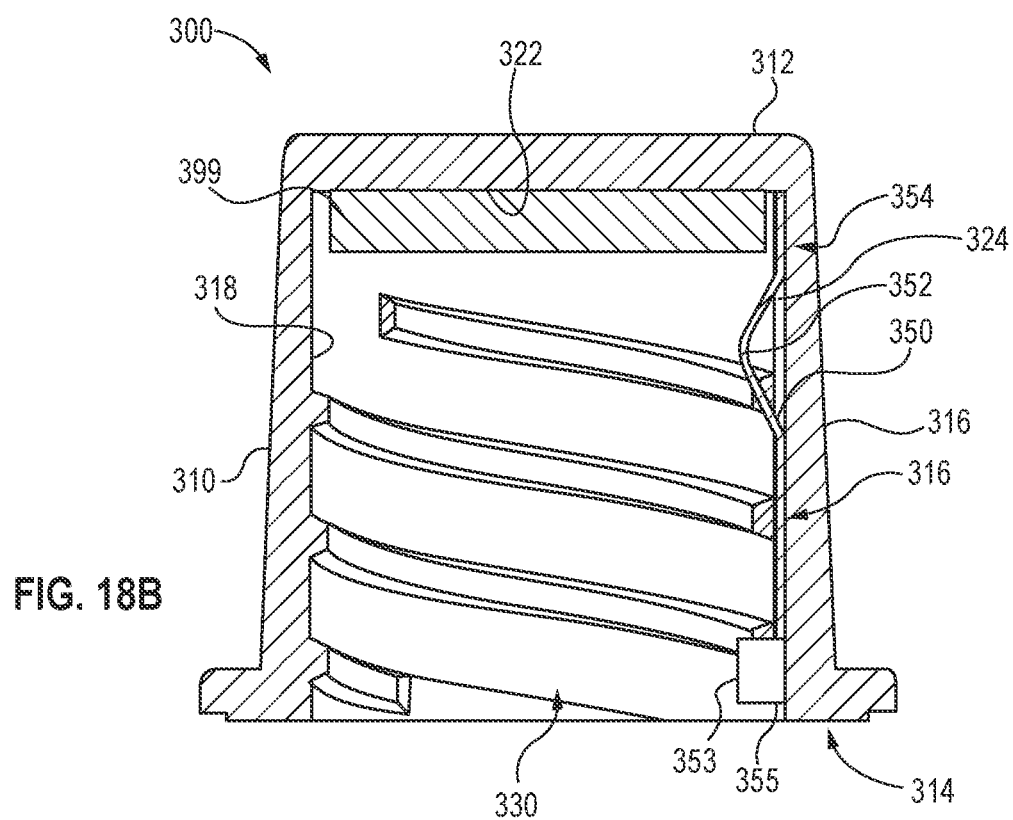
FIG. 18B illustrates a cross-sectional view of the housing in the initial state in accordance with the third embodiment as shown in FIG. 17.
Figure 19:
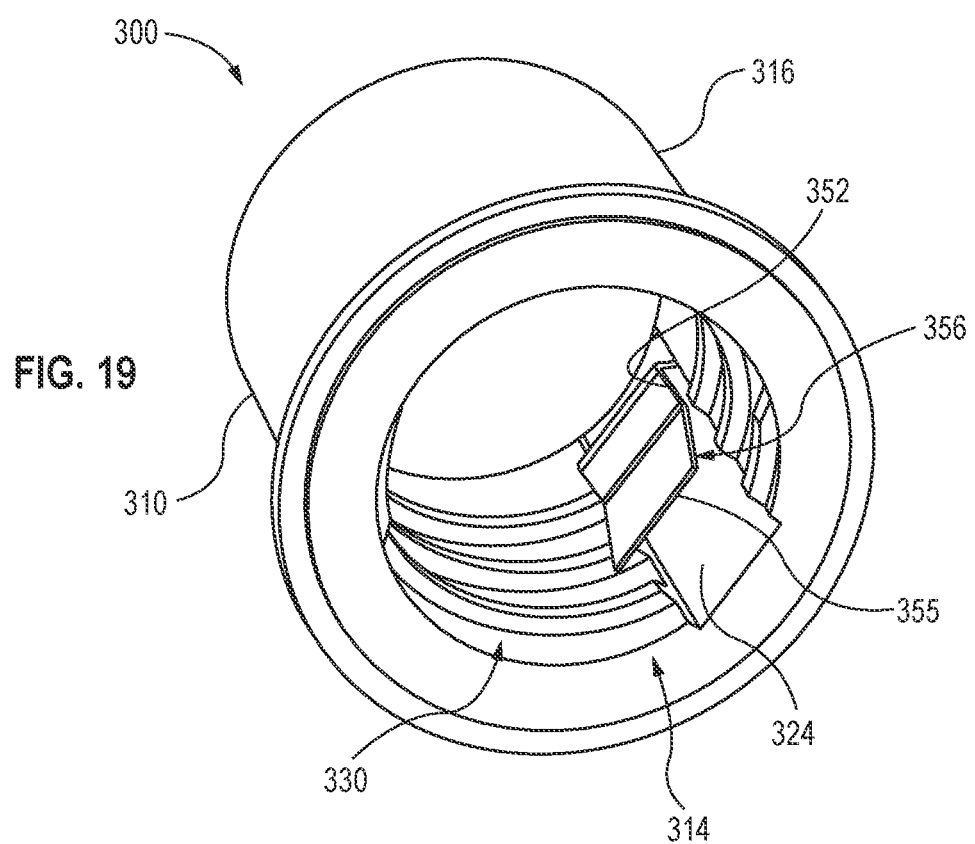
FIG. 19 illustrates a perspective view of the housing in a final state in accordance with the third embodiment as shown in FIG. 17.

A third embodiment of the present disclosure relates to a housing 310 of a medical connector 300. FIGS. 17, 18A and 18B illustrate the medical connector 300 in an initial, un-activated state and FIGS. 19 and 20 illustrate the medical connector 300 in a final, activated state where a corresponding medical connector (not shown) has been fully advanced into a cavity 330 the housing 310.

As shown in FIG. 17 through 18B, the medical connector 300 comprises a substantially cylindrical housing 310 having a distal wall 312, a proximal open end 314, a sidewall 316 extending between the distal wall 312 to the open end 314 and a cavity 330. The cavity 330 extends from the open end 314 to the distal wall 312. In one or more embodiments, an absorbent material 399 in the form of a disk is disposed within the cavity 330, abutting an inner distal surface 322 of the distal wall 312. An inner sidewall surface 318 of the sidewall 316 includes a channel 324 extending from the distal wall 312 to the open end 314. On the inner sidewall surface 318, the channel 324 has a substantially rectangular profile, while the channel 324 extends a depth into the sidewall 316. The depth of the channel 324 is configured to at least partially interdigitate with a spring 350 as discussed in further detail below.

The housing further includes a plurality of threads 320 disposed on the inner sidewall surface 318, however the plurality of threads 320 are not disposed on the channel 324. The plurality of threads 320 are configured to thread with a corresponding thread 82 of a female needleless connector 80 of one of the previous embodiments (as seen in FIGS. 11 and 12).

As shown in FIGS. 17 though 18B, and as best shown in FIG. 18B, the spring 350 is configured as a leaf spring having a rectangular cross-section and an arc 352. In one or more embodiments, the arc 352 is pointed, forming a ramp. The arc 352 is between a distal portion 354 and a proximal portion 356. The distal portion 354 is non-removably attached to the channel 324, while the proximal portion 356 is not attached to the channel 324 and may freely deflect. In operation, the proximal portion 356 abuts the channel 324 in the initial state, as shown in FIGS. 17-18B. As the needleless connector 80 is advanced into the cavity 330, the least one thread 82 depresses the arc 352 of the spring 350 into the channel 324. Depression of the arc 352 cause the proximal portion 354 of the spring 350 to deflect outward, away from the channel 324. In the fully advanced position as shown in FIGS. 19 and 20, a proximal end 355 of the proximal portion 354 of the spring 350 engages a lower segment of the least one thread 82 of the needleless connector 80, thereby locking the needleless connector 80 within the cavity 330 in a threaded fit and an interference fit. In one or more embodiments, the needleless connector 80 is removably locked within the cavity 330. In one or more embodiments, the needleless connector 80 is non-removably locked within the cavity 330 by means of configurations of the spring 350 including, but not limited to, utilizing a stiffer spring.

In embodiments where the needleless connector 80 is removable from the cavity 330, the spring 350 does not return to the initial state, thereby preventing re-use of the housing 310.

In some embodiments, when the needleless connector 80 is fully advanced into the cavity 330 and the spring 350 engages corresponding thread 82, an audible click or sound is created and is detectable by the clinician or ancillary detection systems to indicate that the needleless connector 80 is fully advanced into the cavity 330.

In some embodiments, the proximal end 355 of the spring 350 further comprises a set of tabs 353 protruding from the proximal end 355. In some embodiments, the set of tabs 353 are in the form of a C-clip. In the fully advanced position, the set of tabs 353 interlock with a thread of the corresponding needleless connector 80. The set of tabs 353 engage the thread of the needleless connector 80 to non-removably lock the corresponding needleless connector 80. In some embodiments, the set of tabs 353 is wider than the spring 350. In some embodiments, the set of tabs 353 is configured to de-thread from the corresponding thread 82 and jump off the thread path to prevent re-use.

Figure 21B:
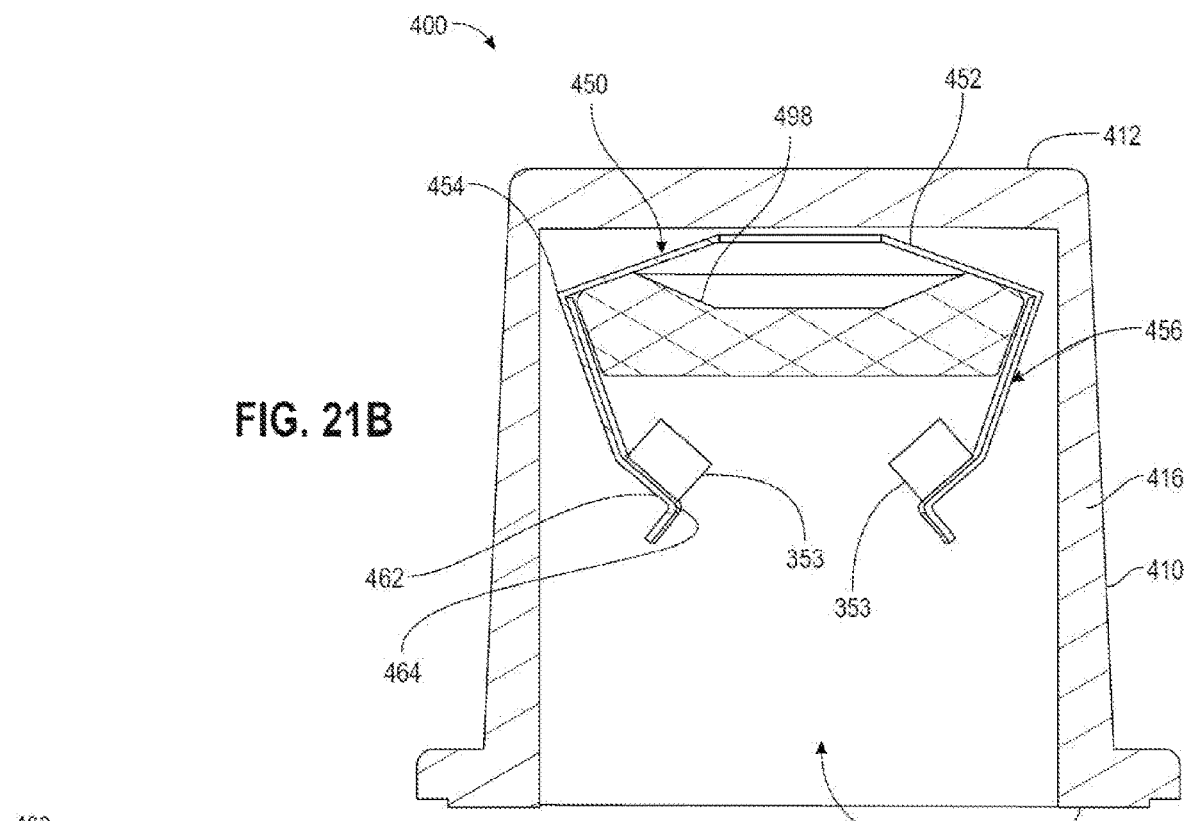
FIG. 21B illustrates a cross-sectional view of the housing in the initial state in accordance with a fourth embodiment as shown in FIG. 21A.

A fourth embodiment of the present disclosure relates to a housing 410 of a medical connector 400. FIGS. 21A and 21B illustrate the medical connector 400 in an initial, un-activated state and FIG. 22 illustrates the medical connector 400 in a final, activated state where a needleless connector (not shown) has been fully advanced into a cavity 430 the housing 410.

As shown in FIGS. 21A and 21B, the medical connector 400 comprises a substantially cylindrical housing 410 having a distal wall 412, a proximal open end 414, a sidewall 416 extending between the distal wall 412 to the open end 414 and a cavity 430. The cavity 430 extends from the open end 414 to the distal wall 412. A cupped spring 350 (also known in the art as a Belleville spring) is disposed within the cavity 330, wherein an open distal end 352 of the cupped spring 350 abuts an inner distal surface 422 of the distal wall 412 of the housing 410.

The cupped spring 450 comprises a frusto-conical shaped disk body 452 having at least two prongs 456 extending from a proximal edge 454 of the disk body 452. While the dimensions of the frusto-conical shape of the disk body 452 determine the spring constant and spring characteristics generally, the at least two prongs 456 may have different spring constant and spring characteristics in relation to the disk body 452. In one or more embodiments, the at least two prongs 456 have a stiffer spring constant and spring characteristics in relation to the disk body 452. In one or more embodiments, the at least two prongs 456 are rigid.

The at least two prongs 456 extend from a proximal edge 454 of the disc body 452 in a proximal direction. Each of the at least two prongs 456 comprise a proximal portion 458 and a distal portion 460 adjacent to the proximal portion 458. The distal portion 460 forms a medial hook 462 extending toward a center of the disk body 452. The medial hook 562 comprises a medial edge 464 configured to engage with a corresponding thread 82 of a corresponding needleless luer connector 80 of one of the previous embodiments (as seen in FIGS. 11 and 12). In one or more embodiments, an absorbent material 498 in the form of a disk is disposed within the cavity 430. The absorbent material 498 abuts a proximal surface of the disk body 452.

Figure 22A:
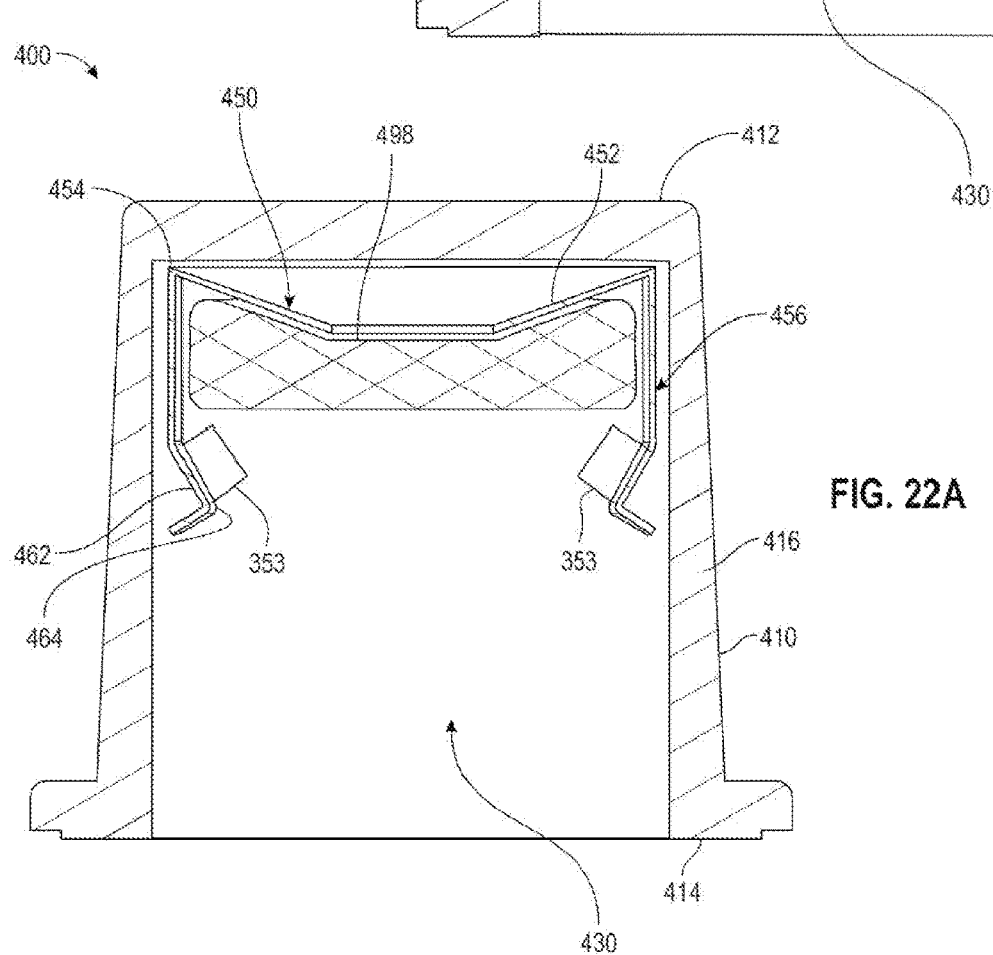
FIG. 22A illustrates a cross-sectional view of the housing in a final state in accordance with a fourth embodiment as shown in FIG. 21A.
Figure 22B:
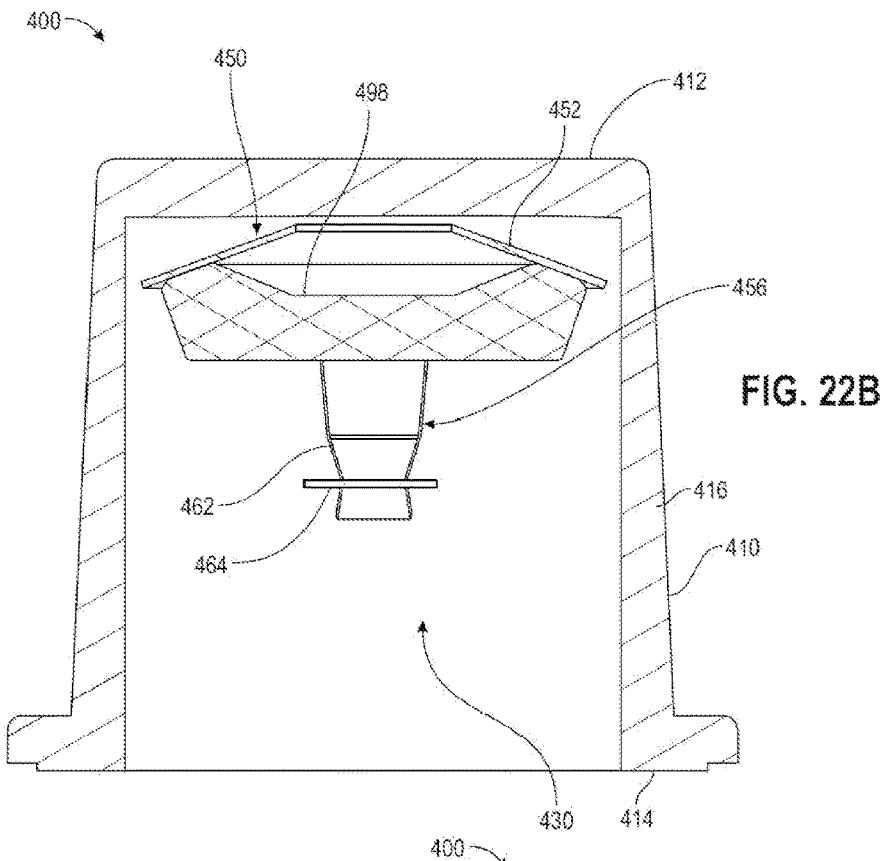
FIG. 22B illustrates a cross-sectional view of the housing in a final state in accordance with a fourth embodiment as shown in FIG. 21A.
Figure 22C:
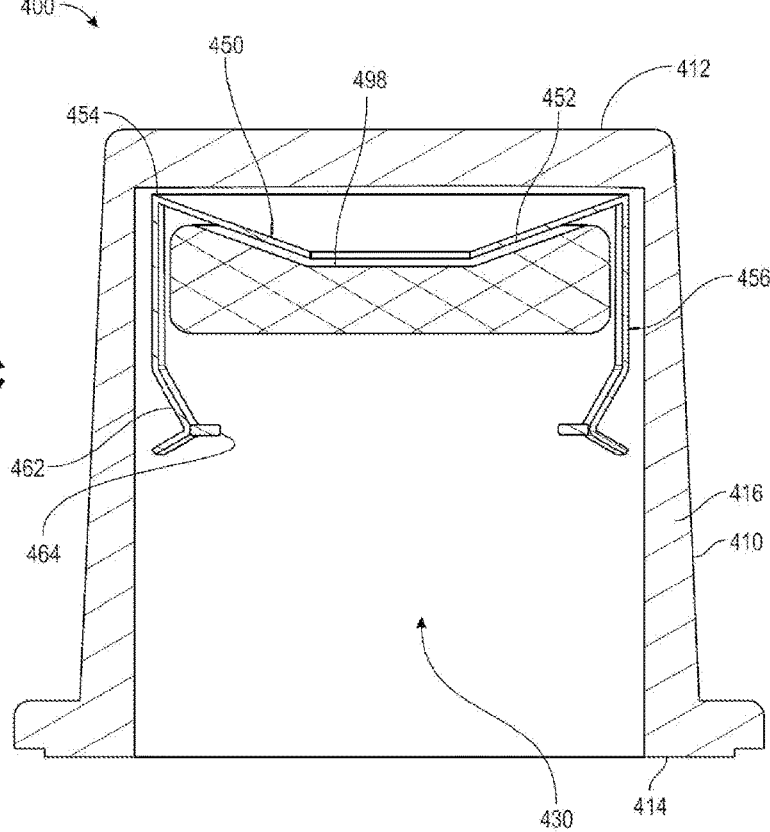
FIG. 22C illustrates a cross-sectional view of the housing in a final state in accordance with a fourth embodiment as shown in FIG. 21A.

FIGS. 21A and 21B illustrate the medical connector 400 in an initial, un-activated state and FIGS. 22A through 22C illustrate the medical connector 400 in a final, activated state where a needleless connector (not shown) has been fully advanced into a cavity 430 the housing 410. In operation, the hub 84 of the corresponding needleless connector 80 of one of the previous embodiments (as seen in FIGS. 11 and 12) is advanced into the cavity 430 of the housing 410. As the hub 84 comes into contact and advances against the disk body 452, the disk body 452 deforms from the initial state of FIGS. 21A and 21B to the final state of FIG. 22A through 22C. The disk body 452 deforms inward, pushing the proximal edge 454 of the disk body 452 in a proximal direction, thereby causing the least two prongs 456 to advance in a proximal direction, whereby the medial hook 462 is further advanced in a lateral direction. In the final state, the medial hook 462 latches onto the at least one thread 82, thereby locking the needle connector 80 into the housing 410 due to the spring force. In the fully advanced position as shown in FIGS. 19 and 20, a proximal end 355 of the proximal portion 354 of the spring 350 engages a lower segment of the least one thread 82 of the needleless connector 80, thereby locking the needleless connector 80 within the cavity 330 in a threaded fit and an interference fit. In one or more embodiments, the needleless connector 80 is removably locked within the cavity 330. In one or more embodiments, the needleless connector 80 is non-removably locked within the cavity 330 by means of configurations of the spring 350 including, but not limited to, utilizing a stiffer spring. The medial hook 456 in the fully advanced position creates a threaded fit and an interference fit with the at least one thread 82 of the needleless connector 80. In one or more embodiments, the needleless connector 80 is removably locked within the cavity 430. In one or more embodiments, the needleless connector 430 is non-removably locked within the cavity 430 by means of configurations of the spring 450 including, but not limited to, utilizing a stiffer spring.

In embodiments where the needleless connector 80 is removed from the cavity 330, the spring 450 does not return to the initial state, thereby preventing re-use of the housing 310.

As shown in FIG. 22A through 22C, in some embodiments, when the needleless connector 80 is fully advanced into the cavity 430 and the spring 450 engages corresponding thread 82, an audible click or sound is created and is detectable by the clinician or ancillary detection systems to indicate that the needleless connector 80 is fully advanced into the cavity 430.

As shown in 22A, in some embodiments, the medial hook 462 further comprises a set of tabs 453 protruding from the medial hook 462. In some embodiments, the set of tabs 453 are in the form of a C-clip. In the fully advanced position, the set of tabs 453 interlock with a thread of the corresponding needleless connector 80. The set of tabs 653 engage the thread of the needleless connector 80 to non-removably lock the corresponding needleless connector 80. In some embodiments, the set of tabs 353 is wider than the spring 350. In some embodiments, the set of tabs 353 is configured to de-thread from the corresponding thread 82 and jump off the thread path to prevent re-use.

As shown in 22B and 22C, in some embodiments, the medial edge 464 is elongated in a lateral and medial direction. In some embodiments, the medial edge 464 is configured as a c-clip. In the fully advanced position, the medial edge 464 interlocks with a thread of the corresponding needleless connector 80. The elongated medial edge 464 engages the thread of the needleless connector 80 to non-removably lock the corresponding needleless connector 80. In some embodiments, the medial edge 464 is wider than the spring 350. In some embodiments, the medial edge 464 is configured to de-thread from the corresponding thread 82 and jump off the thread path to prevent re-use.

Figure 23A:
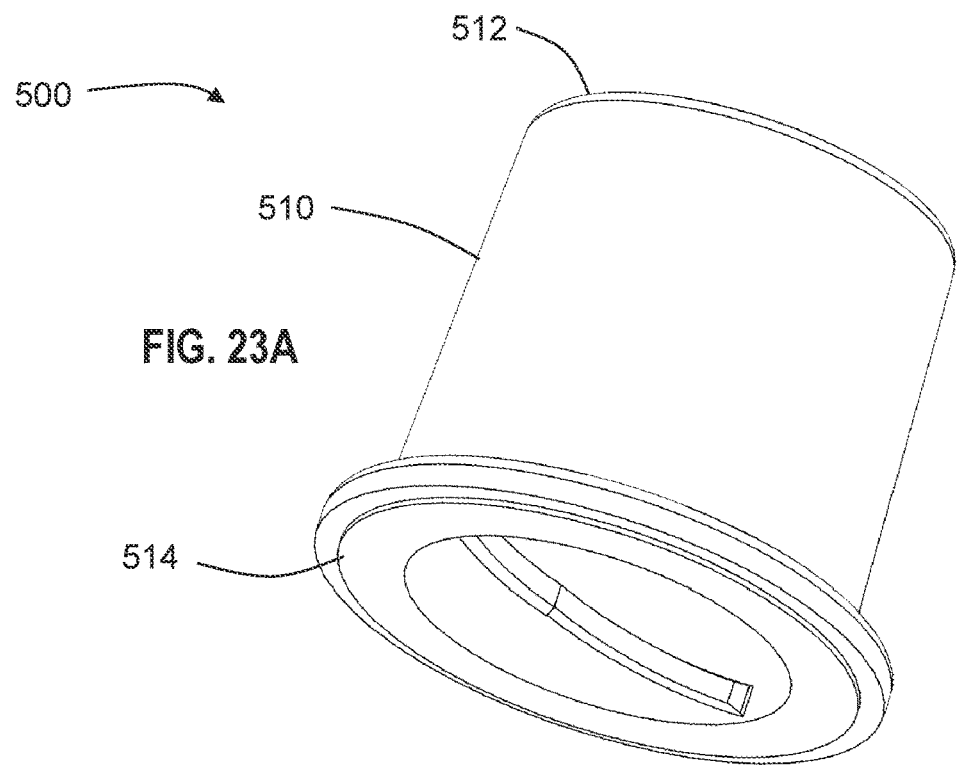
FIG. 23A illustrates a perspective side view of a housing in an initial state in accordance with a fifth embodiment of the present disclosure.
Figure 23B:
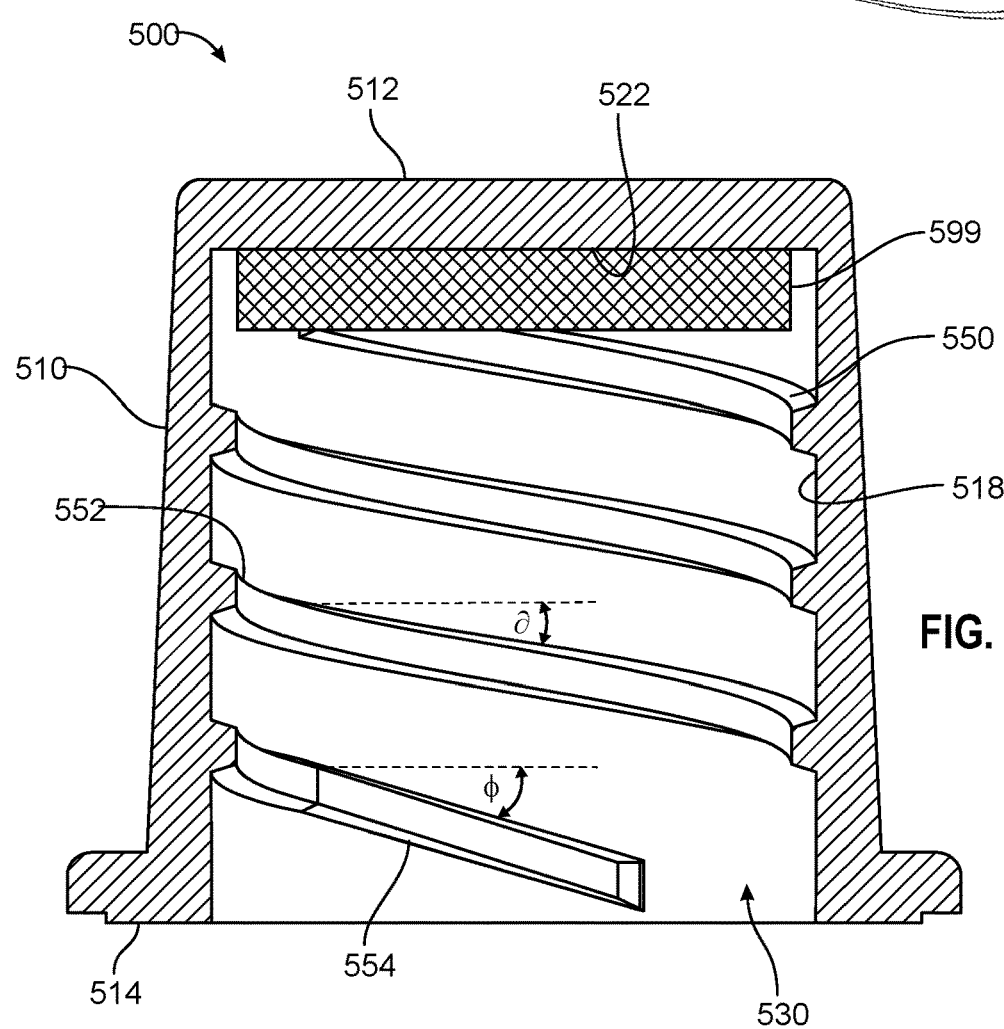
FIG. 23B illustrates a cross-sectional view of the housing in the initial state in accordance with a fifth embodiment as shown in FIG. 23A.
Figure 24A:
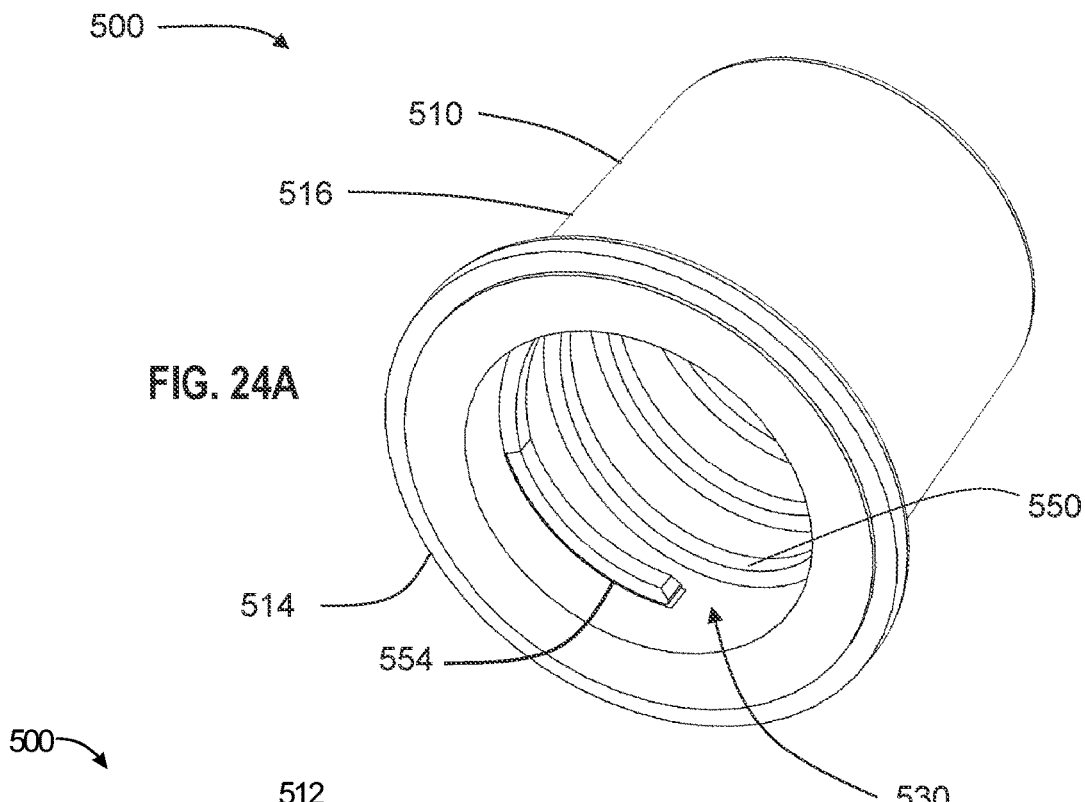
FIG. 24A illustrates a perspective view of the housing in a final state in accordance with a fifth embodiment as shown in FIG. 23A.
Figure 24B:
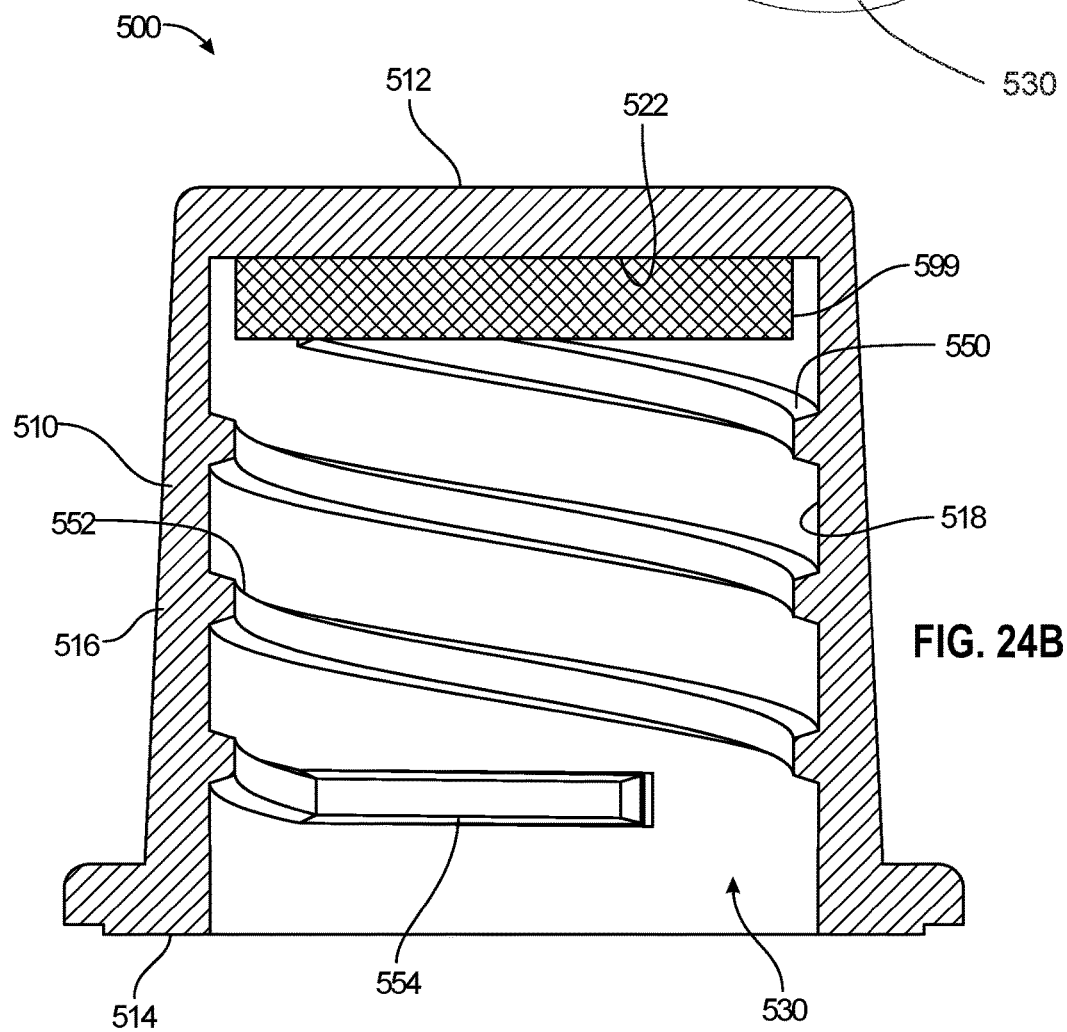
FIG. 24B illustrates a cross-sectional view of the housing in the final state in accordance with a fifth embodiment as shown in FIG. 23A.

A fifth embodiment of the present disclosure relates to a housing 510 of a medical connector 500. FIGS. 23A and 23B illustrate the medical connector 500 in an initial, un-activated state and FIGS. 24A and 24B illustrate the medical connector 500 in a final, activated state where a needleless connector (not shown) has been fully advanced into a cavity 530 the housing 510. In the final state, the needleless connector is removable however the medical connector 500 has integrated features preventing re-use of the medical connector 500, as explained in further detail below.

The medical connector 500 comprises a substantially cylindrical housing 510 having a distal wall 512, a proximal open end 514, a sidewall 516 extending between the distal wall 512 to the open end 514 and a cavity 530. The cavity 530 extends from the open end 514 to the distal wall 512. On an inner sidewall 518 of the cavity 530 at least one helical thread 550 is disposed, the helical thread 550 extending at least partially the length of the inner sidewall 518.

The at least one helical thread 550 comprises a distal portion 552 which is unitarily formed onto the inner sidewall 518 and a frangible portion 554 proximal to the distal portion configured to detach and cross-thread upon threading and advancing a corresponding thread 82 of a corresponding needleless luer connector 80 of one of the previous embodiments (as seen in FIGS. 11 and 12) into the cavity. Upon removal of the luer connector 80, the frangible portion 554 does not return to the initial state, thereby preventing re-use of the housing 510.

In one or more embodiments, the frangible portion 554 in the initial state as shown in FIG. 23B does not follow the thread pattern of the at least one helical thread 550. In one or more embodiments, as shown in FIG. 23B, the frangible portion 554 has a greater approach angle Ø than the approach angle ∂ of the distal portion 552 of the at least one helical thread 550. The greater approach angle Ø is configured to cause deformation of the frangible portion 554. Deformation of the frangible portion 554 prevents re-use of the needleless connector 500 due to thread miss-alignment. Removal of the corresponding needleless luer connector 80 does not return the frangible portion 554 to the original angle Ø of the frangible portion 554, and thus the medical connector 500 cannot be reused. Specifically, as shown in FIG. 24B, insertion and subsequent removal of the corresponding needleless luer connector 80 causes frangible portion 554 to have a near-zero approach angle, whereby the frangible portion 554 is substantially parallel to the inner distal surface 522 of the housing 510.

In one or more embodiments, and as specifically shown in FIG. 23B, the frangible portion 554 extends a quarter turn. In one or more embodiments the frangible portion 554 extends a half turn. In one or more embodiments the frangible portion 554 extends a three quarter turn.

In one or more embodiments, absorbent material 599 is placed in the cavity 530, the absorbent material 599 abutting an inner distal surface 522 of the housing 510. Insertion of a corresponding needleless connector 80 compresses the absorbent material 599, thereby releasing disinfectant into the cavity 530.

Figure 25A:
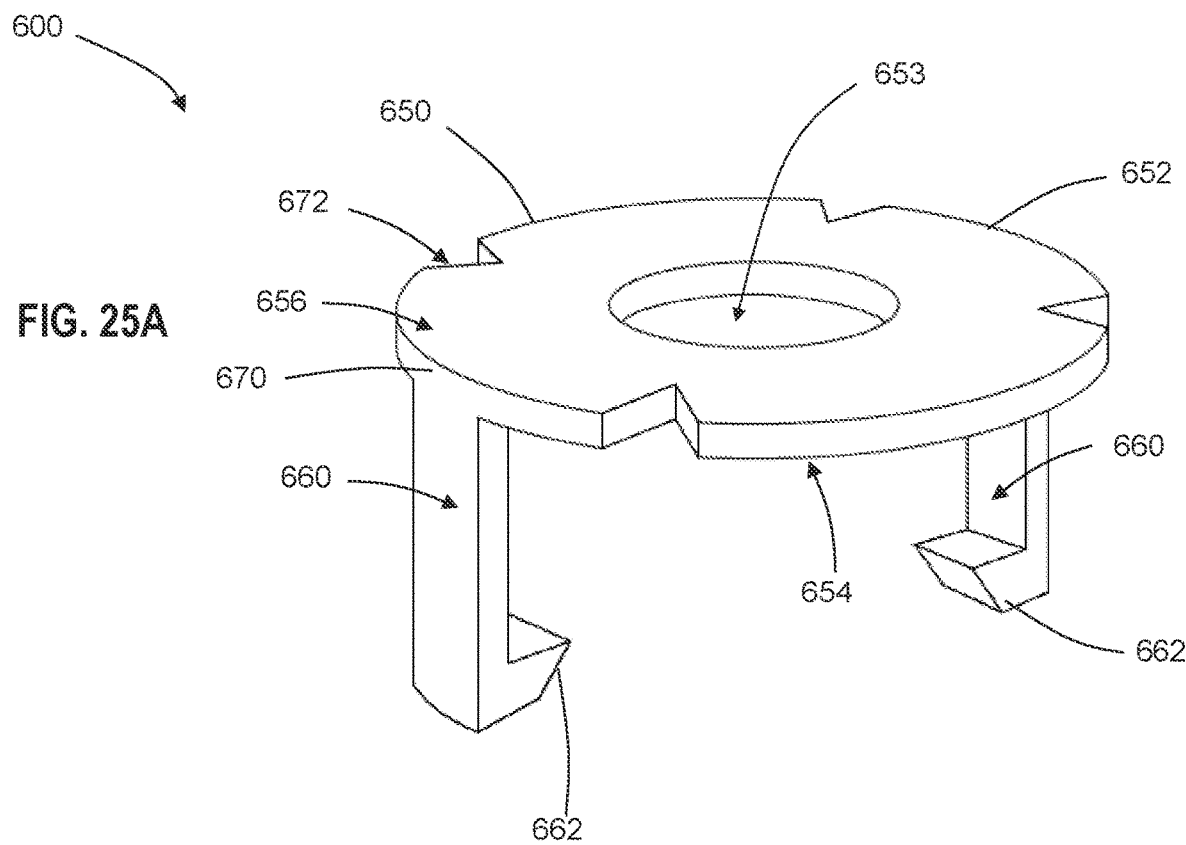
FIGS. 25A and 25B illustrate perspective views of an insert in accordance with a sixth embodiment of the present disclosure.
Figure 25B:
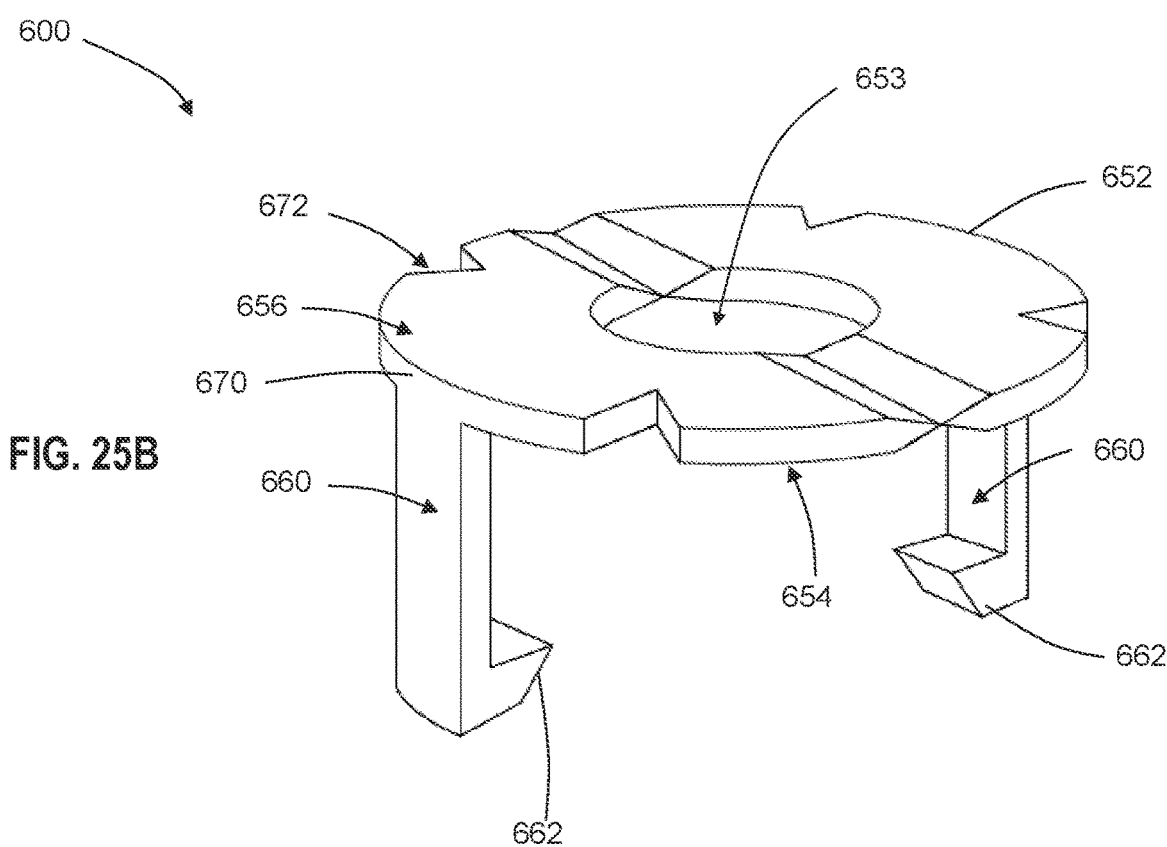

A sixth embodiment of the present disclosure relates to an insert 650 disposed within a housing 610 of a medical connector 600. FIGS. 25A and 25B illustrate embodiments of the insert 650 and FIG. 26 illustrates the medical connector 600 in an initial, un-activated state. In a final, activated state, as described in further detail below, a needleless connector (not shown) is fully advanced into a cavity 630 the housing 610.

As shown in FIGS. 25A and 25B, insert 650 has a generally discoid body 652 having a proximal surface 654 and a distal surface 656. From the proximal surface 654 extend at least two locking tabs 660, the at least two locking tabs 660 extending from the distal surface 256 in a distal direction away from the distal surface 656 of the discoid body 652. Each of the at least two locking tabs 660 comprise a hooked proximal end 662. The hooked proximal end 662 is configured to interlock with corresponding thread 82 of a corresponding needleless luer connector 80 of one of the previous embodiments (as seen in FIGS. 11 and 12) upon threading and advancing the corresponding thread of a corresponding needleless luer connector into the cavity.

In one or more embodiments, the discoid body 652 further includes an aperture 653 disposed on the proximal surface 654 of the discoid body 652, the aperture 653 extending therethrough. The center of the aperture 653 is concentric with the center of the discoid body 652. As shown in FIG. 26 and as explained in further detail below, the aperture 653 is configured to non-removably interlock with a hooked protrusion 640 of the housing 610.

In one or more embodiments, the discoid body 652 further includes a plurality of ridges 672 disposed on a sidewall 670 of the discoid body 652. The plurality of ridges 672 extend into the discoid body 652 in a medial direction from the sidewall 670 of the discoid body 652. As shown in FIG. 26 and as explained in further detail below, the plurality of ridges 672 are configured to interdigitate with at least one tooth 634 of the housing 610.

In one or more embodiments, as shown in FIG. 25B, the discoid body 652 further includes a living hinge 676 disposed across the discoid body 652. As shown in FIG. 26 the living hinge 676 is configured to bend the discoid body 652. Bending of the discoid body 652 causes the least two locking tabs 660 to threads of a medical connector.

As shown in FIG. 26, the medical connector 600 comprises a substantially cylindrical housing 610 having a distal wall 612, a proximal open end 614, a sidewall 616 extending between the distal wall 612 to the open end 614 and a cavity 630. The cavity 630 extends from the open end 614 to the distal wall 612. In one or more embodiments, an absorbent material (not shown) in the form of a disk is disposed within the cavity 630, abutting an inner distal surface 622 of the distal wall 612.

In one or more embodiments, a hooked protrusion 640 extends concentrically from the inner distal surface 622 of the housing 610. The hooked protrusion 640 is configured to non-removably interlock with the aperture 653 of the discoid body 652 upon full advancement of the discoid body 652 into the cavity 630 of the housing 610, thereby preventing re-use of the medical connector 600.

In one or more embodiments, at least one tooth 634 extends medially into the cavity 630 from an inner sidewall 618. The at least one tooth 634 is positioned a distance from the inner distal surface 622 of the housing 610. In one or more embodiments, the at least one tooth 634 is positioned substantially parallel to a proximal end 641 of the hooked protrusion 640. The at least one tooth 634 and the plurality of ridges 672 of the discoid body 652 are configured to interdigitate with one another, wherein the at least one tooth 634 and the plurality of ridges 672 have substantially corresponding shapes. In one or more embodiments, the at least one tooth 634 has a substantially triangular shape and the plurality of ridges 672 have a corresponding triangular profile. In one or more embodiments, at least one ledge 637 is disposed on the inner distal surface 622 of the housing 610.

As shown in FIG. 26, the medical connector 600 is in an initial position. Upon full advancement of the corresponding needleless luer connector 80, the hooked protrusion 640 is received within the aperture 653 of the discoid body 652. However, full advancement is inhibited by misalignment of the plurality or ridges 672 and the at least one tooth 634. Thus, full advancement can occur when the plurality of ridges 672 align with the at least one tooth 634. In the final state, the insert 650 is non-removably locked due to the hooked protrusion 640 being received within the aperture 653 of the discoid body 652.

In one or more embodiments, absorbent material (not shown) is placed in the cavity 630, the absorbent material abutting the inner distal surface 622 of the housing 610.

Insertion of a corresponding needleless connector 80 compresses the absorbent material, thereby releasing disinfectant into the cavity 630.

As shown in FIG. 27, a seventh embodiment of the present disclosure relates to a medical connector 700 comprising of a housing 710 and an insert 750 disposed within the housing 710. As explained in further detail below, the insert 750 is of a resilient and flexible material and comprises at least two living hinges 760 to grip onto a thread 82 of a corresponding needleless luer connector 80 of one of the previous embodiments (as seen in FIGS. 11 and 12).

The housing 710 has a substantially cylindrical shape and comprises a distal wall 712, a proximal open end 714, a sidewall 716 extending between the distal wall 712 to the open end 714 and a cavity 730. The cavity 730 extends from the open end 714 to the distal end 712. In one or more embodiments, an absorbent material (not shown) in the form of a disk is disposed within the cavity 730, abutting an inner distal surface 722 of the housing 710. In one or more embodiments, the distal end 712 of the housing 710 is in the shape of a medially facing hook.

The insert 750 comprises a C-shaped body 752 having a distal end 754 in the form of an arc and an open proximal end 756. From the distal end 754 extend the two living hinges 760. The two living hinges 760 are in the form of cantilevered prongs. As the corresponding needleless luer connector 80 is advanced into the cavity 730, the C-shaped body 752, including the distal end 754 and the living hinges 760, deflect. The resilient material of the insert 750 causes the corresponding needleless luer connector 80 to be retained by the open proximal end 756 of the insert 750. The two living hinges 760 provide a countering force against the C-shaped body 752 of the insert.

In one or more embodiments, absorbent material (not shown) is placed in the cavity 730, the absorbent material abutting an inner distal surface 722 of the housing 510. Insertion of a corresponding needleless connector 80 compresses the absorbent material, thereby releasing disinfectant into the cavity 730.

Figure 28A:
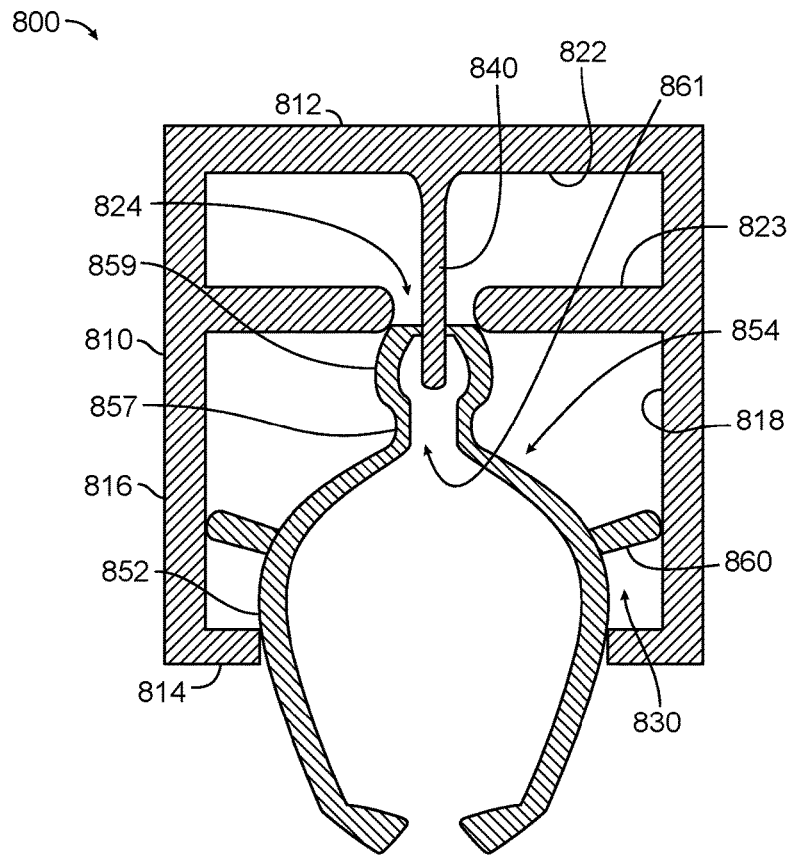
FIGS. 28A and 28B illustrate a cross-sectional view of an insert disposed within a housing of an exemplary medical connector in accordance with an eighth embodiment of the present disclosure.
Figure 28B:
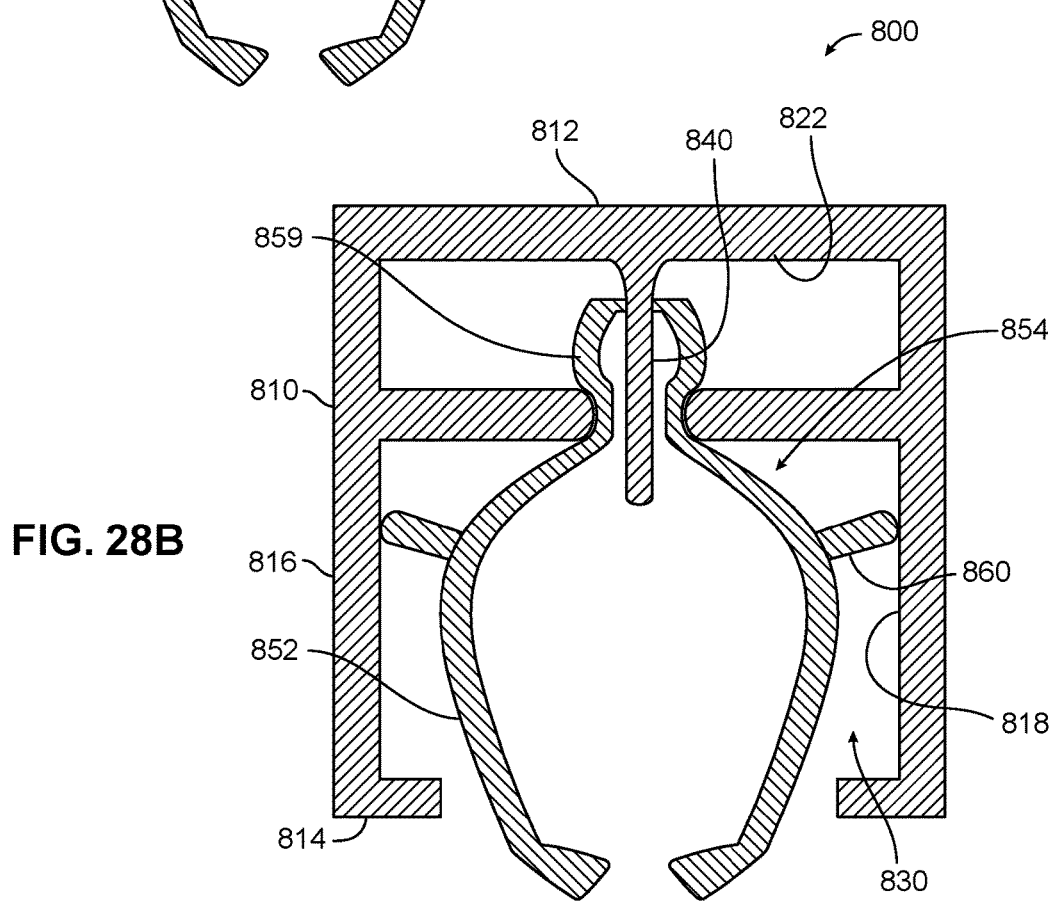

As shown in FIGS. 28A and 28B, an eighth embodiment of the present disclosure relates to a medical connector 800 comprising of a housing 810 and an insert 850 disposed within the housing 810. As explained in further detail below, the insert 850 is of a resilient and flexible material and at least two living hinges 860 to grip onto a thread 82 of a corresponding needleless luer connector 80 of one of the previous embodiments (as seen in FIGS. 11 and 12).

The housing 810 has a substantially cylindrical shape and comprises a distal wall 812, a proximal open end 814, a sidewall 816 extending between the distal wall 812 to the open end 814 and a cavity 830. The cavity 830 extends from the open end 814 to the distal wall 812. In one or more embodiments, an absorbent material (not shown) in the form of a disk is disposed within the cavity 830, abutting an inner distal surface 822 of the distal wall 812. In one or more embodiments, the distal wall 812 further protrudes in a medial direction.

In one or more embodiments, a protrusion 840 extends concentrically from the inner distal surface 822 of the housing 810. The protrusion 840 is configured to non-removably interlock with an aperture 853 of the C-shaped body 852 upon full advancement of the C-shaped body 852 into the cavity 830 of the housing 810, thereby preventing re-use of the needleless connector 800. The protrusion 840 is configured to aid in alignment and advancement of the insert 850 into the cavity 830 of the housing 810.

In one or more embodiments, a medial wall 823 is positioned a distance from the inner distal surface 822 of the housing 810. The medial wall 823 further includes an aperture 824 configured to receive a distal portion 854 of the insert 850 explained in further detail below.

The insert 850 comprises a C-shaped body 852 having a distal portion 854 in the form of an arc and an open proximal end 856. Tangential to the distal portion 854 extend at least two living hinges 860. The two living hinges 860 are in the form of cantilevered prongs. As the corresponding needleless luer connector 80 is advanced into the cavity 830, the C-shaped body 852, including the distal portion 854 and the at least two living hinges 860, deflect. The resilient material of the insert 850 causes the corresponding needleless luer connector 80 to be retained by the open proximal end 856 of the insert 850. The two living hinges 860 provide a countering force against the C-shaped body 852 of the insert.

In one or more embodiments, the C-shaped body 852 further includes a stem 857 having a cylindrical profile extending in a distal direction from the distal portion 854. From the stem extends a bulbous protrusion 859. The C-shaped body 852, stem 857 and the bulbous protrusion 859 form a unitary body through which an aperture 861 extends. The aperture 861 is configured to receive the protrusion 840 of the housing 810 while the stem 857 and the bulbous protrusion 859 are configured to interlock with the aperture 824 of the housing 810.

As the corresponding needleless luer connector 80 is advanced into the cavity 830, the C-shaped body 852, including the distal portion 854 and the living hinges 860, deflect. The resilient material of the insert 850 causes the corresponding needleless luer connector 80 to be retained by the open proximal end 856 of the insert 850. The two living hinges 860 provide a countering force against the C-shaped body 852 of the insert.

In one or more embodiments, absorbent material (not shown) is placed in the cavity 830, the absorbent material abutting the medial wall 823 of the housing 510. Insertion of a corresponding needleless connector 80 compresses the absorbent material, thereby releasing disinfectant into the cavity 830.

In one or more embodiments, the corresponding medical connector may be selected from the group consisting essentially of needle-free connectors, catheter luer connectors, stopcocks, and hemodialysis connectors. In one or more embodiments, the needleless connector is selected from a Q-Syte connector, MaxPlus, MaxPlus Clear, MaxZero, UltraSite, Caresite, InVision-Plus, Safeline, OneLink, V-Link, ClearLink, NeutraClear, Clave, MicroClave, Micro-Clave Clear, Neutron, NanoClave, Kendall, Nexus, InVision, Vadsite, Bionector, etc.

In one or more embodiments, the male connector may be an intravenous tubing end, a stopcock or male lock luer.

In some embodiments, the connector comprises a needleless injection site, which may sometimes be referred to as a needleless injection port, hub, valve, or device, or as a needleless access site, port, hub, valve, or device, and which can include such brands as, for example, Clave® (available from ICU Medical, Inc.), SmartSite® (available from Cardinal Health, Inc.), and Q-Syte™ (available from Becton, Dickinson and Company). In some embodiments, the needleless connector can be connected with any of a variety of different needleless injection sites, such as those previously listed. In one or more embodiments, after the needleless connector has been coupled with connector, it is unnecessary to disinfect (e.g., treat with an alcohol swab) the connector prior to each reconnection of the connector with another connector, as the connector will be kept in an uncontaminated state while coupled with the needleless connector. Use of the needleless connector replaces the standard swabbing protocol for cleaning connectors.

Such connectors are generally and commonly used as catheter and other fluid-tight protective connectors in medical applications. In one or more embodiments, medical connector (100, 200, 300, 400, 500, 600, 700, 800) provides a protective cover for a corresponding needleless luer connector when engaged with the connector when threads from the corresponding needleless luer connector engage and form a releasable connection with the medical connector (100, 200, 300, 400, 500, 600, 700, 800)

The medical connector (100, 200, 300, 400, 500, 600, 700, 800) is made from any of a number of types of plastic materials such as polycarbonate, polypropylene, polyethylene, polyethylene terephthalate, polylactide, acrylonitrile butadiene styrene or any other moldable plastic material used in medical devices. In one or more embodiments, the medical connector (100, 200, 300, 400, 500, 600, 700, 800) comprises a polypropylene or polyethylene material.

The medical connector (100, 200, 300, 400, 500, 600, 700, 800) can achieve disinfection when used on luer connectors by integrating disinfectant in the cavity (130, 230, 330, 430, 530, 630, 730, 830). The disinfectant or antimicrobial agent can be directly included in the absorbent material or disinfectant or antimicrobial agent can be absorbed into sponges or foam material that fills the cavity (130, 230, 330, 430, 530, 630, 730, 830). Medical connector (100, 200, 300, 400, 500, 600, 700, 800) is designed to be compatible in interacting with various disinfectants. In one or more embodiments, the disinfectant or antimicrobial agent may include variations of alcohol or chlorhexidine. In one or more embodiments, the disinfectant or antimicrobial agent is selected from the group consisting essentially of isopropyl alcohol, ethanol, 2-propanol, butanol, methylparaben, ethylparaben, propylparaben, propyl gallate, butylated hydroxyanisole (BHA), butylated hydroxytoluene, t-butyl-hydroquinone, chloroxylenol, chlorhexidine, chlorhexidine diacetate, chlorhexidine gluconate, povidone iodine, alcohol, dichlorobenzyl alcohol, dehydroacetic acid, hexetidine, triclosan, hydrogen peroxide, colloidal silver, benzethonium chloride, benzalkonium chloride, octenidine, antibiotic, and mixtures thereof. In a specific embodiment, the disinfectant or antimicrobial agent comprises at least one of chlorhexidine gluconate and chlorhexidine diacetate. In one or more embodiments, the disinfectant or antimicrobial agent is a fluid or a gel.

In one or more embodiments the absorbent material is a nonwoven material, foam, or a sponge. In a specific embodiment, the absorbent material is polyethylene foam. The foam may be open celled, semi-opened or closed celled and may be molded or extruded or die cut from sheeting. In one or more embodiments, the absorbent reservoir material is molded or extruded or die cut from sheeting to form a cylindrical block shape A peelable seal minimizes entry of potential particulate hazard and also provides a substantially impermeable enclosure for the medical connector (100, 200, 300, 400, 500, 600, 700, 800), provides a leak prevention and protection enclosure, protects the contents of absorbent material contained within the cavity (130, 230, 330, 430, 530, 630, 730, 830), and/or maintains a sealed, sterilized environment. The peelable seal provides a sufficient seal at a range of temperatures, pressures, and humidity levels. In one or more embodiments, the peelable seal comprises an aluminum or multilayer polymer film peel back top. In a specific embodiment, the peelable seal is heat-sealed or induction sealed to the end face of the locking lid or to the needleless connector open end. In one or more embodiments, the peelable seal comprises a moisture barrier.

In some embodiments, the medical connector is configured as a cap containing disinfectant within a cavity of the housing and capable of blocking the lumens of corresponding medical connectors to minimize ingress of disinfectant and microbial agents into connectors, thereby reducing risk of the disinfectant and microbial agents entering the blood stream of a patient.

While the present disclosure has been shown and described with reference to certain exemplary embodiments thereof, it will be understood by those skilled in the art that various changes in form and details may be made therein without departing from the spirit and scope of the embodiments of the present disclosure. For example, a disinfection sponge can comprise any suitable disinfecting or other application-specific substance, and can be made of any suitable material. Also, the inner and/or the outer housing of the medical connector can be single shot molded, or made by other suitable process. Furthermore, any of the features or elements of any exemplary implementations of the embodiments of the present disclosure as described above and illustrated in the drawing figures can be implemented individually or in any combination(s) as would be readily appreciated by skilled artisans without departing from the spirit and scope of the embodiments of the present disclosure.

In addition, the included drawing figures further describe non-limiting examples of implementations of certain exemplary embodiments of the present disclosure and aid in the description of technology associated therewith. Any specific or relative dimensions or measurements provided in the drawings other as noted above are exemplary and not intended to be limiting.

Reference throughout this specification to "one embodiment," "certain embodiments," "one or more embodiments" or "an embodiment" means that a particular feature, structure, material, or characteristic described in connection with the embodiment is included in at least one embodiment of the disclosure. Thus, the appearances of the phrases such as "in one or more embodiments," "in certain embodiments," "in one embodiment" or "in an embodiment" in various places throughout this specification are not necessarily referring to the same embodiment of the disclosure. Furthermore, the particular features, structures, materials, or characteristics may be combined in any suitable manner in one or more embodiments.

Although the disclosure herein has provided a description with reference to particular embodiments, it is to be understood that these embodiments are merely illustrative of the principles and applications of the present disclosure. It will be apparent to those skilled in the art that various modifications and variations can be made to the method and apparatus of the present disclosure without departing from the spirit and scope of the disclosure. Thus, it is intended that the present disclosure include modifications and variations that are within the scope of the appended claims and their equivalents.

What is claimed is:
1. A medical connector comprising:
a housing having a single, substantially cylindrical housing body having a radial protrusion extending from the substantially cylindrical housing body and a cavity within the substantially cylindrical housing body that is defined by a distal closed end, a proximal open end, a partially cylindrical inner sidewall of the substantially cylindrical housing body and a radial inner sidewall of the radial protrusion, the radial inner sidewall of the radial protrusion has a larger diameter than the partially cylindrical inner sidewall of the substantially cylindrical housing body;
a locking structure disposed on the radial inner sidewall of the radial protrusion, the locking structure including a sloped tab, wherein a locking position is being defined by the sloped tab and a first position disposed circumferentially adjacent to the sloped tab;
an insert advanceable into, and rotatable from the first position to the locking position within the cavity of the substantially cylindrical housing body, the insert comprising a discoid body having a distal surface, a proximal surface, a peripheral sidewall and a cantilever locking tab extending proximally from the peripheral sidewall, the cantilever locking tab defining an inner wall facing the cavity and an outer wall facing the radial inner sidewall of the radial protrusion, the insert including at least one thread disposed on the inner wall of the cantilever locking tab for direct mating, threaded engagement with a corresponding thread formed on a corresponding medical connector inserted within the cavity, and a recessed notch disposed on a proximal portion of the outer wall of the locking tab, the notch opposing the sloped tab when the locking tab is rotated to the locking position; and
an absorbent material disposed between the distal surface of the insert and an inner top surface of the cavity of the housing, such that the absorbent material does not make direct contact with a corresponding medical connector, the absorbent material containing a disinfectant, wherein insertion of the corresponding medical connector into the cavity compresses the absorbent material, thereby releasing disinfectant into the cavity.

2. The medical connector of claim 1, wherein the recessed notch of the insert engages a ledge of the sloped tab of the locking structure when the recessed notch is advanced past the sloped tab during insert rotation.

3. The medical connector of claim 2, wherein an audible click or sound is created when the recessed notch is advanced past the ledge of the sloped tab.

4. The medical connector of claim 1, wherein the locking structure further includes an outwardly sloped surface that adjoins the sloped tab, which slopes radially outwardly from the radial inner sidewall toward the cavity and extends circumferentially from the first position to the locking position.

5. The medical connector of claim 4, wherein the outwardly sloped surface contacts the outer wall of the locking tab and causes deformation of the locking tab toward the cavity.

6. The medical connector of claim 1, wherein the locking structure further includes a proximally sloped surface that incorporates the sloped tab, the proximally sloped surface located adjacent to a ledge of the sloped tab, the proximally sloped surface slopes inwardly with respect to the radial inner sidewall of the radial protrusion from a distal position to a proximal position thereupon, wherein the recessed notch of the insert engages the ledge when the recessed notch is advanced past the sloped tab during insert rotation.

7. The medical connector of claim 1, wherein the distal surface of the insert abuts an inner top surface of the cavity of the housing when the insert is fully advanced into the cavity.

8. The medical connector of claim 1, wherein fully advancing the insert into the cavity in a distal direction causes the distal surface of the insert and the inner top surface of the cavity of the housing to compress the absorbent material, the absorbent material releasing the disinfectant.

9. The medical connector of claim 8, wherein the disinfectant evacuates into the cavity by a gap defined by the partially cylindrical inner sidewall of the housing and the peripheral sidewall of the insert.

10. The medical connector of claim 1, wherein a diameter of the partially cylindrical inner sidewall of the housing is larger than a corresponding diameter of the peripheral sidewall of the insert.

11. The medical connector of claim 1, wherein a retention tab is disposed on an inner top surface of the housing, the retention tab non-removably securing thereabout a through aperture disposed on the distal surface of the insert.

12. A medical connector comprising:
a housing having a single, substantially cylindrical housing body having a radial protrusion extending from the substantially cylindrical housing body and a cavity within the substantially cylindrical housing body that is defined by a distal closed end, a proximal open end, a partially cylindrical inner sidewall of the substantially cylindrical housing body and a radial inner sidewall of the radial protrusion, the radial inner sidewall of the radial protrusion has a larger diameter than the partially cylindrical inner sidewall of the substantially cylindrical housing body;
a locking structure disposed on the radial inner sidewall of the radial protrusion, the locking structure including a sloped tab; and
an insert advanceable into the cavity of the housing body, the insert comprising a discoid body having a distal surface, a proximal surface, a peripheral sidewall and a cantilever locking tab extending proximally from the peripheral sidewall, the locking tab defining an inner wall facing the cavity and an outer wall facing the radial inner sidewall, the insert including at least one thread disposed on the inner wall of the cantilever locking tab for direct mating, threaded engagement with a corresponding thread formed on a corresponding female needleless connector inserted within the cavity, and a recessed notch disposed on a proximal portion of the outer wall of the cantilever locking tab, wherein threading the female needleless connector into the cavity causes the insert to be advanced into the cavity, and causes the recessed notch to oppose and engage the sloped tab;
an absorbent material disposed between the distal surface of the insert and an inner top surface of the cavity of the housing, such that the absorbent material does not make direct contact with the corresponding female needleless connector, the absorbent material containing a disinfectant, wherein insertion of the corresponding female needleless connector into the cavity compresses the absorbent material, thereby releasing disinfectant into the cavity.

13. The medical connector of claim 12, wherein the female needleless connector is removably threaded into the cavity.

* * * * *